United States Patent
Söderlund et al.

(10) Patent No.: US 8,895,292 B2
(45) Date of Patent: Nov. 25, 2014

(54) MICROFLUIDIC CHIP DEVICES AND THEIR USE

(75) Inventors: Hans Söderlund, Espoo (FI); Ari Hokkanen, Espoo (FI); Kari Kataja, Espoo (FI); Ingmar Stuns, Espoo (FI); Kai Kolari, Espoo (FI); Heli Siren, Espoo (FI); Stella Rovio, Espoo (FI); Reetta Satokari, Espoo (FI); Jan Rautio, Espoo (FI)

(73) Assignee: Valtion Teknillinen Tutkimuskeskus, Espoo (FI)

( * ) Notice: Subject to any disclaimer, the term of this patent is extended or adjusted under 35 U.S.C. 154(b) by 708 days.

(21) Appl. No.: 12/421,252

(22) Filed: Apr. 9, 2009

(65) Prior Publication Data
US 2009/0269767 A1    Oct. 29, 2009

(30) Foreign Application Priority Data

Apr. 10, 2008 (FI) .................................... 20085299

(51) Int. Cl.
| | |
|---|---|
| C12M 1/34 | (2006.01) |
| C12Q 1/68 | (2006.01) |
| G01N 33/48 | (2006.01) |
| B01L 3/00 | (2006.01) |
| G01N 33/543 | (2006.01) |
| G01N 35/00 | (2006.01) |

(52) U.S. Cl.
CPC ..... *G01N 33/54326* (2013.01); *B01L 2200/027* (2013.01); *B01L 2200/0668* (2013.01); *B01L 3/50273* (2013.01); *B01L 2200/10* (2013.01); *B01L 3/502761* (2013.01); *B01L 2200/0684* (2013.01); *G01N 33/54366* (2013.01); *B01L 2400/088* (2013.01); *B01L 2300/0636* (2013.01); *B01L 2300/087* (2013.01); *G01N 35/0098* (2013.01); *B01L 2300/0681* (2013.01); *B01L 2300/16* (2013.01); *B01L 2400/086* (2013.01); *B01L 2200/0652* (2013.01)
USPC ......... 435/287.1; 435/6.1; 422/68.1; 422/501

(58) Field of Classification Search
None
See application file for complete search history.

(56) References Cited

U.S. PATENT DOCUMENTS

| | | | | |
|---|---|---|---|---|
| 5,587,128 A | * | 12/1996 | Wilding et al. | ................. 422/50 |
| 5,965,410 A | * | 10/1999 | Chow et al. | ................. 435/91.2 |

(Continued)

FOREIGN PATENT DOCUMENTS

| | | |
|---|---|---|
| EP | 1 792 655 A1 | 6/2007 |
| WO | WO 0185341 A1 | 11/2001 |

(Continued)

OTHER PUBLICATIONS

Pamme et al "On-chip free-flow magnetophoresis: Continuous flow separation of magnetic particles and agglomerates" Anal. Chem, 2004, 76: 7250-7256.*

(Continued)

*Primary Examiner* — Betty Forman
(74) *Attorney, Agent, or Firm* — Arent Fox LLP

(57) ABSTRACT

A microfluidic chip device (MCD) and its use for performing miniaturized assays on magnetic microbeads (MMs) are described. The MCD is particularly useful for carrying out miniaturized transcript analysis by aiding affinity capturing (TRAC) assays, including PCR. The MCD comprises at least one reaction chamber with sealable liquid connections and at least one fluidic pillar filter in each chamber. The fluidic pillar filter comprises rods with spacings allowing MMs to pass. The sealable liquid connections feed liquid to the reaction chamber, wherein air bubbles are removed. The liquid stream contacts the MMs, which are manipulated with a magnetic rod. The liquid connections enable trapping of the MMs behind the pillar filters or in the channel, while the liquid is changed.

15 Claims, 10 Drawing Sheets

(56) References Cited

U.S. PATENT DOCUMENTS

| | | | |
|---|---|---|---|
| 7,641,863 B2 * | 1/2010 | Doktycz et al. | 422/503 |
| 2003/0134416 A1 * | 7/2003 | Yamanishi et al. | 435/372 |
| 2005/0250221 A1 | 11/2005 | Horita | |

FOREIGN PATENT DOCUMENTS

| WO | WO 02093125 A2 | 11/2002 |
|---|---|---|
| WO | WO 2006/032044 A2 | 3/2006 |
| WO | WO 2007/000401 A1 | 1/2007 |
| WO | WO 2007035498 A2 | 3/2007 |
| WO | WO 2008/007270 A2 | 1/2008 |
| WO | WO 2008/094198 A2 | 8/2008 |

OTHER PUBLICATIONS

Liu Y-J et al.; "A micropillar-integrated smart microfluidic device for specific capture and sorting of cells"; Electrophoresis; Nov. 2007; vol. 28; p. 4713-4722.

Wang Y-J et al.; Study of a novel microfluidic DNA extraction chip; Weinadianzi Jishu; Oct. 2007; vol. 44; No. 9; p. 853-856, 867 (abstract).

* cited by examiner

MICROFLUIDIC CHIP DEVICES AND THEIR USE

RELATED APPLICATION INFORMATION

This application claims priority to Finnish Patent Application No. 20085299, filed on Apr. 10, 2008. This foreign priority application is incorporated herein by reference in its entirety.

TECHNICAL FIELD OF THE INVENTION

The present invention is related to microfluidics, particularly to microfluidic chip devices for performing binding assays, including PCR-reactions, with one or a plurality of binding partners using several adsorption and desorption steps on magnetic microbeads. Also disclosed are methods for manipulating magnetic microbeads in said microfluidic chip devices as well as the use of said microfluidic chip device and method for manipulating magnetic microbeads for increasing the sensitivity and efficacy of micro-scale binding assays performed on magnetic microbeads.

BACKGROUND OF THE INVENTION

Microfluidics is a technology dealing with diminutive amounts of flowing liquid solutions, which are fed through microchannels placed on microchips. Said technology is rapidly emerging as a new, more sensitive alternative to the powerful oligomer-chip technology.

The microfluidic systems have been used for purification, separation or sequencing and include methods such as microcapillary electrophoresis, packed bed immuno- or enzyme-reactors (U.S. Publ. Appl. No. 2002/0023841, U.S. Publ. Appl. No. 2004/0094419, PCT Publ. Appl. No. WO 2005/09481, PCT Publ. Appl. No. WO 03/099438, and PCT Publ. Appl. No. WO 2007/035498). Microfludic devices with pillar filters are described in PCT Publ. Appl. No. WO 2008/024070, PCT Publ. Appl. No. WO 01/85341, PCT Publ. Appl. No. WO 2007/098027, PCT Publ. Appl. No. WO 99/09042, and PCT Publ. Appl. No. WO 02/093125, as well as in Liu et al., Electrophoresis, November 2007, vol. 28, 4173-4722), but automation and miniaturizing of binding assays are also suggested. Conventional binding assays usually take place in solution and include reactions between binding partners and their counterparts which together form binding pairs. Examples of binding pairs are antibodies and antigens or complementary probe and target sequences. In a typical binding assay the binding partners of the binding pairs are alternating between solid and liquid phases with intermediate purification and extraction stages, which are performed on microbeads.

In the patent literature, few of the problems encountered in miniaturizing conventional binding assays are discussed, but it is evident that magnetic particles, which are very convenient in macroscale conventional binding assays, are not quite as easy to manipulate when used in microfluidic applications. This is probably a reason why magnetic microbeads have been used mainly for concentration and isolation by retaining them within certain regions of microchannels having a diameter smaller than that of the microbead. Microfluidic pillars have also been used in microfluidic channel systems as mechanical stoppers of microbeads. The adsorption and desorption reactions between the partners of the binding pairs as well as the purification stages, require application of thorough and efficient mixing systems in order to allow sufficient contact between the target binding partners in the sample and their counterparts on the surface of microbeads or vice versa. Therefore, in prior art, the adsorption/desorption steps and purification steps are generally carried out before feeding the liquid stream with processed target binding partners into the microfluidic channel system for subsequent separation and detection. In order to obtain adequate mixing in microfluidic systems the application of physical forces, such as acoustic forces have been suggested, but methods particularly aiming at manipulation of magnetic microbeads in the microfluidic channels are not suggested.

Gas bubble generation caused by electrical fields in aqueous solutions is discussed in U.S. Publ. Appl. No. 2006/0228749, and various physical forces are suggested for handling the problem, but the fact that bubble formation is a frequently encountered difficulty whenever a liquid stream is fed into a microfluidic channel system is not discussed, even if air bubbles in a microscale system, where the volume of a bubble is very big as compared to the volume of the liquids fed into the system, is a problem that can seriously distort any results obtained by using microfluidic methods.

SUMMARY OF THE INVENTION

The object of the present invention is to improve the performance and efficacy of assays by manipulating magnetic microbeads in microfluidic chip devices. Improved efficacy and sensitivity is achieved by the microfluidic microchip device of the present invention, wherein the bubble formation in the liquid stream and clustering of magnetic microbeads is prevented by allowing the liquid stream first to pass a microfluidic pillar filter in a reaction chamber of the microfluidic channel system and thereafter the liquid stream meeting the magnetic microbeads in the channel system are transported through another microfluidic pillar system, thereby disintegrating or disassembling the clustering magnetic microbeads. The applicability of the microfluidic chip device is further increased by providing the device with holes for steering rods on so called steering plate, which together with for example liquid connections and electric needles facilitate exact fitting of further electric and fluidic contacts between the microfluidic chip device and external equipment on a measurement interface. The microfluidic chip device and the measurement interface with the steering plate are all placed on a stabilizing bottom, a so called docking station. The steering rods on the steering plate and the holes on the microchip devices facilitate exact fitting of electric and/or fluidic connections between the external equipment and the microfluidic chip device. This is particularly useful if the microfluidic chip device is not provided with fully integrated means for carrying out binding assays, isolation, concentration, separation, detection, as well as PCR and decrease of background noise caused by redundant detectable label as well as detection of target binding partners or their counterparts forming a binding pair present in the sample to be analyzed.

The present microchip device has liquid connections or junctions and comprises or is connected to electric fields, for controlling conditions, e.g. temperature, surveillance of liquid streams by conductivity, for separating processed reaction products from the binding assay by capillary electrophoresis, magnetic rods for moving magnetic particles and optic instruments for recording the reaction products. The microfluidic channel system comprises one or more sealable tubular channels or passages having ports or liquid connections, which may act both as inlets or outlets and can be closed or opened by said liquid connections or junctions, which are provided with seals. The microchannel system further comprises one or more, preferably two, enlarged reaction chambers or cavities, which are broader or deeper than the tubular channels of the system. The reaction chambers are provided with one or more microfluidic pillar filters for removing bubbles and for disintegrating clusters of magnetic microbeads to which target analytes and further reactants or reagents are attached or may be attached during reactions taking place while the magnetic microbeads are transferred from one part of the channel to another. After a thorough mixing by the transfer the magnetic microbeads with captured reagents, while one solution is removed and replaced by another, the analytes or reactants captured on the magnetic microbeads are trapped on the microfluidic pillar filter or behind it. This trapping prevents the magnetic microbeads from escaping with the drainage flow during the continuous or discontinuous feeding of sample, reagent or washing solutions. The whole microfluidic chip device may be provided in centimeter, millimeter or nanometer scale.

The present invention is particularly related to a microfluidic chip device for manipulating magnetic microbeads in a microfluidic channel system. The microfluidic chip device is either an integrated microfluidic chip device, which is provided with all equipment needed for carrying out all the tasks required in a typical binding assay or it is externally connected through a measurement interface to the equipment needed for carrying out said tasks. The equipment are magnetic, electric, and optic equipment and the tasks include isolation, concentration, binding assays with adsorption and desorption reactions, separation and detection and further include, automatic or semiautomatic recording and software applications for calculating the final results.

In addition to a tubular channel, the microfluidic channel system preferably comprises two reaction chambers (101 and 102), but may comprise only one reaction chamber in which case the microfluidic channel may be used for some of the reaction steps, e.g. PCR-reactions and concentration. The microfluidic channel system is provided with one or more sealable fluidic connections (201, 202 and/or 203), which may be used both as inlets and outlets, while the direction of the flow may be reversed. The liquid streams include sample solutions, reagent solutions, washing solutions, or eluents fed into the system. As shown in FIG. 2, which demonstrates one preferred embodiment of the invention, connection (201) is the inlet, connection (202) the outlet and connection (203) is used to recover the processed liquid solution or to concentrate the solution before leading it to means for separation and detection (600 and 700). The target binding partners recovered after processing may be amplified and/or concentrated before they enter the capillaries used for separation and detection. The liquid connections may be used in a reversed order depending upon the configuration of the microfluidic chip device and the location of, the integrated fluidic, electric and optic equipment provided on the microfluidic chip device as well as the ultimate application of the microfluidic chip device.

In the preferred embodiment of the invention shown in FIG. 2, the microfluidic channel system comprises two reaction chambers (101 and 102), each of which are provided with at least one microfluidic pillar filter (301 and 302). Microfluidic pillar filters are diminutive scaffolds or arrays of quadrangular or round rods (303) as shown in FIG. 3. These scaffolds are placed so that the interspaces or spacings (304) between the rods are bigger than the diameters of the magnetic microbeads. Typically, the interspaces of the microfluidic pillars are in a scale of about 20 µm to about 30 µm, preferably about 25 µm, but naturally the sizes may vary according to the size of the microfluidic chip device.

The preferred magnetic equipment for manipulating magnetic microbeads (401), which tend to form clusters (402) as shown in FIG. 1, comprise an external magnetic rod (403), but may include other electromagnetic forces. By moving the magnetic rod over the microfluidic chip device and the microfluidic pillars therein, the magnetic microbeads are transferred within the microfluidic channel system and clustering is prevented.

The preferred electric equipment comprises electric needles and/or electric thin film elements or thin film pads (501), which act as heating elements (502), temperature measurement elements (503), high voltage elements (504) or conductivity measurement elements (505) The sealable fluidic connections (201, 202 and/or 203) are preferable fluidic connectors with seals (204), but may be injection needles.

The microfluidic channel system are provided with integrated or externally connected separation equipment, such as straight or looped capillary channels for chromatographic separation using capillary electrophoresis with or without an isatachophoresis pre-separation step.

For detection, the microfluidic chip device is provided with integrated or externally connected equipment for detection comprising optic or electric detectors including equipment for measuring fluorescence, UV/VIS absorption, IR, conductivity or refraction index as well as mass spectrometers.

The externally connected microfluidic chip device, which preferably consists of two layers (801 and/or 802) and supports the microfluidic channel system, which is placed between the two layers, is easily connectable by using the perforated holes (804) to the external equipment comprising a measurement interface (901) with a steering plate (902) having steering rods (903). The microfluidic chip device is provided with preferably perforated holes (804), which allow easy and exact contacting between the external equipment, electric needles (501), electric pads (501), fluidic connections (201, 202 and/or 203) and the microfluidic chip device.

In the two chamber microfluidic channel system, the microfluidic pillar filter (301) in one of the reaction chambers (101) prevents bubble formation in the liquid flow fed to the microfluidic channel system and the other microfluidic pillar filter (302) in the other reaction chamber (102) acts as a disintegrator of magnetic microbeads (401) clusters (403). When a single chamber microfluidic channel system is used, the at least one microfluidic pillar filter provided therein may function to both prevent bubble formation and disintegrate microbead clusters. Alternatively, the single chamber microfluidic channel system may include more than one microfluidic pillar filter, where one microfluidic pillar filter prevents bubble formation, and another microfluidic pillar filter disintegrates microbead clusters.

The microfluidic chip device has sealable fluidic couplings, which preferably are fluidic connectors or injection needles constructed for this purpose and which are provided with leakage preventing seals (204).

The invention is above all related to a more effective method for manipulating magnetic microbeads in a microfluidic channel system. This method prevents cluster formation of magnetic microbeads and thereby increases the free reactive surface on the surface of the microbeads. In the method of the invention a liquid stream is fed to a first reaction chamber (101), wherein a microfluidic pillar filter (301) removes air bubbles and subsequently the liquid streams is contacted with magnetic microbeads (401), which when a magnetic rod (403) is switched on, may be forced through a microfluidic pillar filter (302), which disintegrates the clusters formed by the magnetic microbeads (401), which have diameter smaller than the interspaces (304) between the rods (303) in the microfluidic pillar filters (301 and 302).

The present invention is also related to methods for carrying out binding assays using said method for manipulating magnetic microbeads. The binding assays comprise at least one binding reaction between a pair of binding partners or binding moieties on magnetic microbeads and are useful for performing miniaturized immunoassays or hybridization reactions for determining the presence or absence of genomic sequences, mRNA, or ribosomal RNA. The binding assays are not limited to detecting or measuring only one binding pair but can be used for simultaneous determination of plurality of binding pairs, so called multiplexing.

Methods for quantify and detecting one or more polynucleotide sequences, which methods are applicable in microfluidic chip devices are described in U.S. Publ. Appl. No. 2004/0053300, U.S. Pat. No. 7,361,461, U.S. Publ. Appl. No. 2003/0129589, U.S. Publ. Appl. No. 2003/0082530, U.S. Publ. Appl. No. 2006/0035228, U.S. Pat. No. 5,514,543, U.S. Publ. Appl. No. 2005/0214825, U.S. Publ. Appl. No. 2004/0121342, PCT Publ. Appl. No. WO 02/33126, PCT Publ. Appl. No. WO 2004/063700, as well as in the publications Kataja et al, *J Microbiol Methods*, October 2006, vol. 67, 102-113, and in Pirrung et al., *Bioorg Med Chem Lett*, September 2001, vol. 11, 2437-2440. Further conventional binding assays which have been, applied or can be used in microfluidic systems are described in the patent literature (U.S. Publ. Appl. No. 2002/0076825, U.S. Publ. Appl. No. 2002/0123134, U.S. Publ. Appl. No. 2004/0005582, U.S. Publ. Appl. No. 2004/0969960, U.S. Publ. Appl. No. 2006/0228749).

The method also allows detection and determination of the amounts of target sequences and genetic variations including single nucleotide polymorphism (SNP) as described in U.S. Publ. Appl. No. 2009/0011944. The method is particularly adapted for performing transcript analysis by aid of affinity capture (TRAC) assays as described in U.S. Publ. Appl. No. 2004/0053300 and U.S. Pat. No. 7,361,461 and for determining antibodies and antigens as well as fragments thereof.

Throughout this application, various patents and publications have been cited. The disclosures of these patents and publications are hereby incorporated by reference in their entireties into this application, in order to more fully describe the state of the art to which this invention pertains.

DETAILED DESCRIPTION OF THE INVENTION

Figure 1:
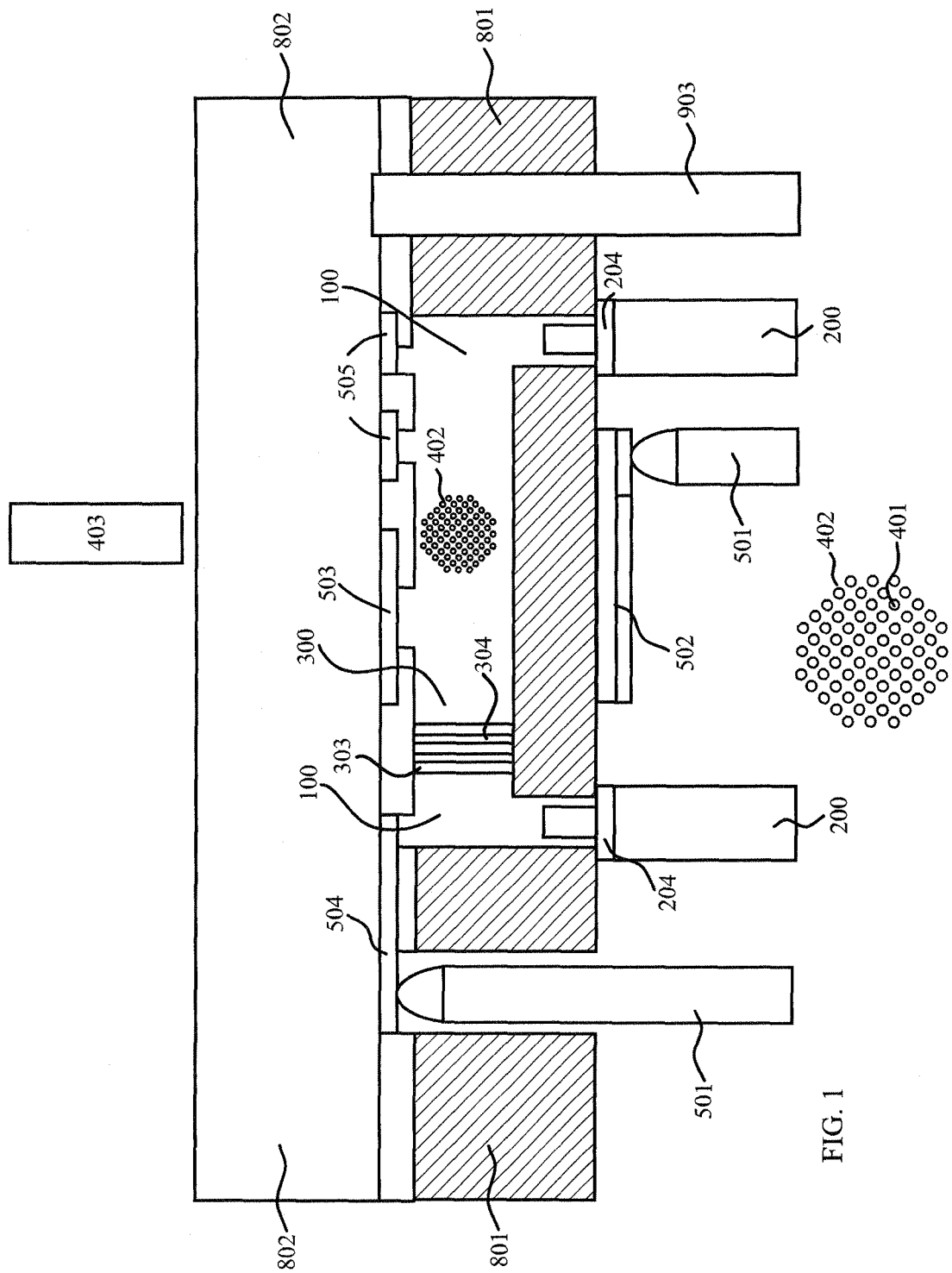
FIG. 1 is a schematic illustration of a cross-section of a microfluidic chip device with fluidic and electric connections and an externally placed magnetic rod for the manipulation of the cluster of microbeads.

When using microfluidic on-chip systems for performing biological solid phase assisted binding assays in connection with magnetic microbeads, the magnetic microbeads have a tendency to cluster. Clustering prevents the target binding partners present in the sample from being efficiently attached to the surface of the magnetic microbeads and also prevented effective purification in the washing steps. In accordance with one aspect of the invention, clusters of magnetic microbeads could be disintegrated or disassembled by forcing the magnetic microbeads through a microfluidic pillar filter. By manipulating said magnetic microbeads their surfaces were liberated and could be contacted from all directions by the surrounding liquid solution flowing through the microfluidic channel system and thereby the reactions between the target binding partners and their counterparts were improved and formation of immobilized binding pairs is increased. The sensitivity of the binding assays was improved. In accordance with another aspect of the invention, improved purification of the immobilized binding pairs on the magnetic microbeads and removal of unbound reactants and solutions was also achieved. Accordingly, the reaction rates could be accelerated and the efficiency of the binding assays was improved leading to more reliable and sensitive results. According to another aspect of the invention, air bubbles were disintegrated when the liquid was transferred through the microfluidic pillars. This solved the problem of distorted results caused by bubble formation.

Another aspect of the invention solves the difficulties that may be encountered in the incorporation of the microfluidic chip devices and the exact fitting of the diminutive liquid junctions, electrodes of the microchip into the microfluidic apparatus. The problem may be solved by providing the microfluidic chip devices of the present invention with perforated holes for steering rods on the measurement interface, which secured the fitting of the junctions, when the holes were adjusted by placing them on the steering rods of the steering plates so as to be penetrated by the injection needles and electric needles at holes provided for said equipment.

A microfluidic chip device is a diminutive microfabricated apparatus wherein micro- or nanoliter volumes of fluid streams including samples, reagents, washing and eluting solutions are manipulated in microchannels on a platform or microchip. Fluid flow is achieved by mechanical force, for example by pressure from micropumps, injectors or by capillary electrophoresis. Microscale fluidic behavior differs from macroscale behavior, and makes the microfluidic chip devices particularly adaptable for so called micro total analyze systems (µ-TAS), including separation, capturing, isolation, focusing, enrichment, concentration, physical disruption, mixing, sequencing, amplification and/or binding assays and reduction of background caused by redundant detector label.

An integrated microfluidic chip device comprises all elements needed to perform sequential solid liquid phase binding and releasing steps in micro-scale structures, which are fabricated in or otherwise closely attached on the microfluidic chip device and include channels, reaction chambers, electrode elements, electromagnetic elements, scaffolds, separation equipment, and optic elements The integrated microfluidic chip devices facilitate physical, biophysical, biological, biochemical, or chemical reactions including binding reactions, adsorption, washing, desorption, multiplication, concentration, separation, detection, etc. The microfluidic chip device is a platform, which supports the fluidic micro-scale structures. It may have various shapes or configurations and it may vary in length, breadth as well as in height or depth. It can be quadratic, rectangular, circular, elliptic, or have another useful irregular shape. The size of the major surface of microfluidic chip device can vary considerably, for example from about 0.5 $cm^2$ to about 10 $cm^2$ with a characteristic dimension from about 1 $cm^2$ to about 5 $cm^2$. The microfluidic chip devices may include channels or reaction chambers fabricated between the surfaces of their layers.

An externally connected microfluidic chip device may be placed in or on a steering plate connected to auxiliary external equipment and connects the microfluidic chip device to external magnetic, electric or optic equipment that control the functions of the microfluidic chip device through the measurement interface supported by a docking station (800). Together the measurement interface and the microfluidic chip device enable total analysis in microliter scale.

The microfluidic chip device may comprise one or more layers, and preferably comprises two layers, a bottom layer and a top layer. The bottom layer may be made of a non-transparent, moldable, solid or semisolid porous or non-porous chip material, such as silicon, rubber, glass, ceramics, plastics, polymers, or copolymers. The upper layer is preferably transparent and may be made of glass, quartz, Pyrex, or borosilicate, but silicon provided with windows may be used as well. Polymer microfabrication, replication techniques, direct fabrication with casting or molding can be used. Optical lithographic patterning including the use of image masking and hot embossing are examples of some applicable systems in microfabrication.

According to one aspect of the invention, the upper and the lower surfaces of the one or more layers of the microfluidic chip device may be provided with depressions, including dents, grooves, recesses and niches. The tubular channels for transporting the liquid solutions can advantageously be fitted in the depressions on the upper side of the lower layer. On the lower side of lower layer, electric circuits and electrodes may be advantageously soldered and located so as to fit to the junctions connecting the microchip device. Different etching schemes are used for producing the depressions for channel shapes. These shapes can also be made by powder blasting, or laser ablation. These methods are, however, not widely used, because etching of the silicon layer is so easy and the preferred bottom layer is usually made of silicon. Preferably the silicon layer is a wafer or a thin slice of semiconducting material, such as a silicon crystal, upon which microcircuits are constructed by doping, diffusion, ion implantation, chemical etching or deposition of various metals. Wafers are of key importance in the fabrication of semiconductors such as integrate circuits, but are also convenient for fabricating microfluidic chip devices.

The two layers of the microfluidic chip device are preferably tightly closed or sealed. According to one aspect of the invention, no leakage from between the layers is allowed. Polydimethylsiloxane (PDMS) is a particularly useful material for closing any channel systems. The layers are welded, pressed, or glued together. Preferred methods are the use of adhesive bonding, thermal bonding, or solvent bonding. The layers are perforated before or after the layers are joined together. The perforated holes are located so as to fit to the microfluidic chip steering plate in the measurement interface with its electric, fluidic, and/or magnetic control equipment as well as the optic detector contacts, everything preferably supported by a docking station.

The microfluidic chip device is a platform, which supports the microfluidic channel system with microchannels, and reaction chambers. The microfluidic channel system is a miniaturized channel system, which comprises elongated tubular channels and reaction chambers in which processes, such as physical, chemical, biological, biophysical or biochemical processes including adsorption and desorption reactions are carried out. The microfluidic channel systems enable fluid streams to be introduced or injected or pumped from an external source and to be processed in said microfluidic channel system, which comprises at least one, but preferably more fluidic or liquid connections or ports acting as inlets and/or outlets and leading to the reaction chambers.

A microfluidic channel system can comprise any material that permits the passage of a fluid through it. Preferably, the channel is a tube made of rubber, Teflon (polytetrafluoroethylene), or another useful material. Preferably, it should be made of a biocompatible material or a material that can be made biocompatible. A microfluidic channel system can be of any dimensions, which depends on the size of the chip device, but generally it is in microscale, ranging from 10 microns up to 1 millimeter in internal diameter.

A channel is a structure in a chip with a lower surface and at least two walls that extend upward from the lower surface of the channel, and in which the length of two opposite walls is greater than the distance between the two opposite walls. A channel therefore allows for flow of a fluid along its internal length. A channel is preferably a covered tunnel.

A reaction chamber is a depression or small cavity or well on the surface of the microfluidic chip device that is capable of containing a liquid or fluid sample. The reaction chamber has a lower surface surrounded on at least two sides by one or more walls that extend from the lower surface of the channel. The walls can be of any form, but generally they extend upward in a sigmoidal, curved or multi-angled fashion. The lower surface of the reaction chamber and the tubular can be at the same level as the upper surface of a chip or higher than the upper surface of a chip, or lower than the upper surface of a chip. The sides or walls of the reaction chamber or channel may be made of other materials than those that make up the lower layer of the chip. In this way the lower surface of the chip can comprise a thin material through which electrical, electromagnetic forces can be transmitted, and the walls of one or more reaction chambers or channels may comprise insulating materials that prevent the transmission of electrical forces. The walls of the reaction chambers and the channel may be made of any material, including silicon, glass, rubber, and/or one or more polymers, plastics, ceramics, or metals. Preferably, the channels and reaction chambers are made of a biocompatible material or a material that can be made biocompatible and wherein the target binding partners and other reactants are manipulated on magnetic microbeads.

Figure 6:
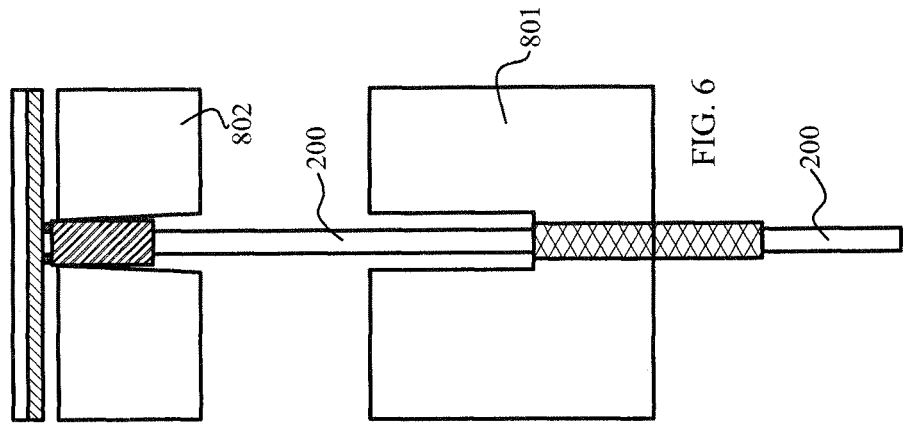
FIG. 6 is a schematic representation of a cross-section of a liquid needle.

A fluidic or liquid connection, which may act both as an outlet or inlet is an opening or port to the microfluidic channel system comprising a tubular channel and one or two reaction chambers through which a fluid sample can enter or exit the chamber. The seal is preferably controlled by electric or magnetic forces or a combination thereof. The port can be of any dimensions, but preferably it is of a shape and size that allows a sample to be transported through the port by physical forces, or dispensed through the port by means of a pipette, syringe, injection needle or other means of applying a sample. Sealable fluidic connections are ports acting as inlets and/or outlets for liquid streams. They can be closed mechanically, or by injection needles, or fluidic connectors specifically constructed for microfluidic systems (U.S. Pat. No. 6,319,476). A typical injector useful in the present invention is shown in FIG. 6.

Microfluidic pillar filters are miniaturized scaffolds comprising a plurality of very small rods fabricated in the microfluidic channel system. Previously, such miniature rods have been used in microfluidic systems as mechanical barriers for retention of microbeads. In the present invention the microfluidic pillar filters are not solely used for retention of microbeads, they are particularly applied for disintegration of clusters of magnetic microbeads and for preventing air bubble formation in the solutions fed into the channel system. The rods, which may be quadruples or may have round, elliptic or oval cross-sections may be made in macro-, micro- or nano-size and may have a height of approximately from one to five millimeter and the diameter of its cross-section, which can be circular or quadratic, is from approximately 20 micrometer to approximately one millimeter. Naturally, the size depends upon the size of the microfluidic chip device and can be in micrometer dimension as well. In accordance with one aspect of the invention, the microfluidic pillar filters of the present invention preferably have interspaces, which are bigger than the diameters of the magnetic microbeads and allow them to pass through the barrier.

The magnetic microbeads may be manipulated with magnetic forces exerted by any suitable magnetic apparatus. Magnetic forces are forces exerted on magnetic microbeads by a magnetic field, which may be provided, for example, by a magnetic rod. In accordance with one aspect of the present invention, the preferred magnetic equipment for manipulating magnetic microbeads may be an external magnetic rod. In the present invention manipulation of the magnetic microbeads replaces mixing with any mechanical or acoustic means for mixing. Sufficient movement of the separated magnetic microbeads and the solution in the channel system is achieved in order to allow sample, reagent or any other solution to contact the surface of microbead and any substance immobilized on its surface from all directions. By using the magnetic rod, which forces the magnetic microbeads through the pillar filters in the reaction chambers, the components, in the samples, reagents and other solutions and the surface of the magnetic microbeads become sufficiently interspersed.

Magnetic forces refer to the forces acting on a magnetic microbead due to the application of a magnetic field. Particles have to be magnetic or paramagnetic to provide sufficient magnetic forces for manipulation of the particles. A typical magnetic particle is made of super-paramagnetic material. When the particle is subjected to a magnetic field a magnetic dipole is induced in the magnetic microbead or particle. To achieve a sufficiently large magnetic manipulation force, the volume susceptibility of the magnetic microbeads should be maximized, the magnetic field strength should be maximized, and the magnetic field strength gradient should be maximized.

In the present invention paramagnetic microbeads are preferred, because their magnetic dipoles can be induced by externally applied magnetic fields and returned to zero, when the external field is turned off. Commercially available paramagnetic or other magnetic microbeads may be used. These commercially available magnetic microbeads have sizes from $0.5\mu$ to $10\mu$ or more. They may have different structures and compositions. Magnetic microbeads may have ferromagnetic materials encapsulated in thin latex or polystyrene shells. Another type of magnetic particles has ferromagnetic nanoparticles diffused in the latex or polystyrene surroundings. The surfaces of both these particle types are polystyrene in nature and may be modified to link to various types of molecules. They can for example be affinity labeled or covered with avidin or streptavidin, or some other affinity label.

The manipulation of magnetic microbeads requires the magnetic field distribution to be generated over microscopic scales. One approach, for generating such magnetic fields, is the use of microelectromagnetic units. Such units can induce or produce a magnetic field, when an electrical current, is applied. The switching on/off status and the magnitudes of the electrical current applied to these units will determine the magnetic field distribution. The structure and dimension of the microelectromagnetic units may be designed according to the requirement of the magnetic field distribution. Manipulation of magnetic microbeads includes the directed movement, focusing and trapping of magnetic microbeads. Theories and practice regarding the motion of magnetic microbeads in a magnetic field as well as applications thereof may be found in the literature, including text books.

As is evident from the description provided herein, the aim of the present invention is to provide a novel and inventive method for manipulating magnetic microbeads, but it does not exclude the use of electric equipment in the microfluidic chip device In accordance with one aspect of the invention, electric equipment may include electric connections, particularly electric needles or electric thin film elements or electric pads. The electric thin film elements may act as heating elements, temperature measurement elements, high voltage elements or conductivity measurement elements. The thin film pads are generally round but may have any other shape. Electrodes can also comprise doped semiconductors, where a semiconducting material is mixed with small amounts of other conductive materials.

In the present invention electrical forces may be used for separation, for example in capillary electrophoresis. Electric forces may also be used for the heating and temperature measurements used when performing PCR-reactions, but temperature adjustment and control are also important in all kinds of bioassays. This is achieved by attaching electric connection on both sides of the reaction chamber or the tubular channel electric contact pads, by which the sample can be heated and the temperature measured. Particularly, if the electric connections are attached on both sides of the channel, a constant electric field is achieved by aid of which both sample and magnetic microbeads may be moved. A pair of electric pads or electrodes may also be used for concentration of target partners before capillary electrophoresis.

Dielectrophoresis may be used for performing binding assays with antigen and antibodies and chemicals having affinity for each other. A dielectrophoretic force is the force that acts on a polarizable particle in a non-uniform electrical field. Conventional dielectrophoresis is the movement of polarized microbeads in non-uniform electrical fields. There are generally two types of dielectrophoresis, positive dielectrophoresis and negative dielectrophoresis. In positive dielectrophoresis, particles are moved by dielectrophoresis toward the strong field regions. In negative dielectrophoresis, particles are moved by dielectrophoresis toward weak field regions. Whether microbeads with immobilized target partners exhibit positive or negative dielectrophoresis depends on whether the magnetic microbeads are more or less polarizable than the surrounding medium.

The separation equipment in the microfluidic channel system is provided with integrated or externally connected chromatographic equipment comprising straight or looped channels performing electrophoresis with or without isotachophoresis as a pre-separation step. Capillary electrophoresis is particularly convenient in the present invention. Isotachophoresis is a technique used in analytical chemistry to separate charged particles. It is a further development of electrophoresis. It is a powerful separation technique using a discontinuous electrical field to create sharp boundaries between the sample constituents. In isotachophoresis the sample is introduced between a fast leading electrolyte and a slow terminating electrolyte. After application of an electric potential a low electrical field is created in the leading electrolyte and a high electrical field in the terminating electrolyte. The pH at sample level is determined by the counter-ion of the leading electrolyte that migrates in the opposite direction. In the first stage the sample constituents migrate at different speeds and start to separate from each other. The faster constituents will create a lower electrical field in the leading part of the sample zone and vice versa. Finally the constituents will completely separate from each other and concentrate at an equilibrium concentration, surrounded by sharp electrical field differences. Specific spacer or marker molecules are added to the sample to separate physically the sample constituents of interest. Isotachophoresis shows its superiority to conventional separation techniques when the maximum resolution is achieved with the latter. The choice of the experimental parameters remains complex, but selection of appropriate parameters may be made by consulting reference materials known to those skilled in the art.

In the present invention, optic equipment includes means for surveillance of the movement of target partners and for measuring or detecting the target partners after a completed binding assay has been performed. For detection, the microfluidic channel system may be provided with integrated or externally connected equipment comprising detectors including fluorescence detectors, laser induced fluorescence detectors, mass spectrometers or equipment for measuring UV/VIS absorption, IR, conductivity or refraction index.

The microfluidic chip device of the present invention is preferably an automatic system, which means that the system requires substantially no manual procedures, such as pipetting or manual transfer of samples or reagents, inversion or vortexing of tubes, placing samples in a centrifuge or an incubator by a practitioner. An automated system may, however, require manual application of the sample to the system by pipetting or injecting, or manual recovery of sample components that have been fully processed by the system by collecting from tubes, wherein the reacted flow is collected. An automated system may or may not require a practitioner to control power-driven systems for fluid flow, to control power-driven systems for generating physical forces for the performance of processing and analysis tasks, to control power-driven systems for generating physical forces for the translocation of sample components, and the like, during the operation of the integrated chip system, but these control measures may be computerized. An automated system, such as an automated integrated biochip system of the present invention, is preferably computer-driven.

In the present invention the magnetic field, particularly the magnetic rod, exerts the forces only on magnetic particles and target partners or binding pairs immobilized on magnetic particles. The invention is not applicable to the use of non-magnetic particles, e.g., polystyrene particles or beads. Accordingly the present invention relates to microfluidic chip devices that utilize magnetic microbeads.

According to one aspect of the invention the microfluidic pillar filters are preferably controlled by one or more magnetic rods, which enable the transfer of the magnetic microbeads from one reaction chamber to another, thereby allowing the microbeads to be contacted with fresh sample, reagent and washing solutions. The magnetic microbeads to which analytes and reagents are alternatively attached and released during the feeding of sample, reagent and washing solutions are simultaneously prevented from escaping with the stream of solutions, when the obsolete sample, reagent, washing and other solutions are removed.

The microfluidic chip device, its structure, and its fabrication are described in more detail by referring to the Figures.

FIG. 1 schematically illustrates a cross section of the microfluidic chip device of the present invention. The microfluidic channel system (100) comprises one or two reactions chambers (not distinguishable in FIG. 1) in which magnetic microbeads (401) forming clusters (402) are manipulated. The microfluidic channel system (100) is provided with one or more microfluidic connections or microfluidic needles (200), which preferably are sealable with leakage preventing seals (204). The microfluidic channel system (100) is provided with one or two microfluidic pillar filters. One of the said microfluidic pillar filters (300) with pillars (303) and their interspaces (304) are schematically shown in FIG. 1. Magnetic microbeads (401) forming clusters (402) and a magnetic rod (403) for manipulating the magnetic microbeads (401) are indicated. The microfluidic chip device also comprises electric equipment (500), including two electric needles (501) as well as other electric thin film elements or pads (501). These elements comprise heating elements (502), temperature measurement element (503), high voltage elements (504), and conductivity measurement elements (505). In a preferred embodiment of the invention the microfluidic chip device (800) consists of two layers (801, 802). The bottom layer (801) is preferably a silicon layer in which the microfluidic channel system (100) is embedded and the upper layer is a transparent layer, e.g. a glass-lid (802), which allows monitoring of the stream of components from the binding assays carried out in the microfluidic channel system (100). The lower layer of the chip device is provided with holes (not shown in FIG. 1) for the steering needles (903), electric needles (501) and liquid connections (200) protruding from a steering plate (not shown in FIG. 1). The upper layer (802) of the chip device preferably comprises a straight or looped channel for performing separation (600) (not shown in FIG. 1) and means for detection (700) (not shown in FIG. 1).

Figure 2:
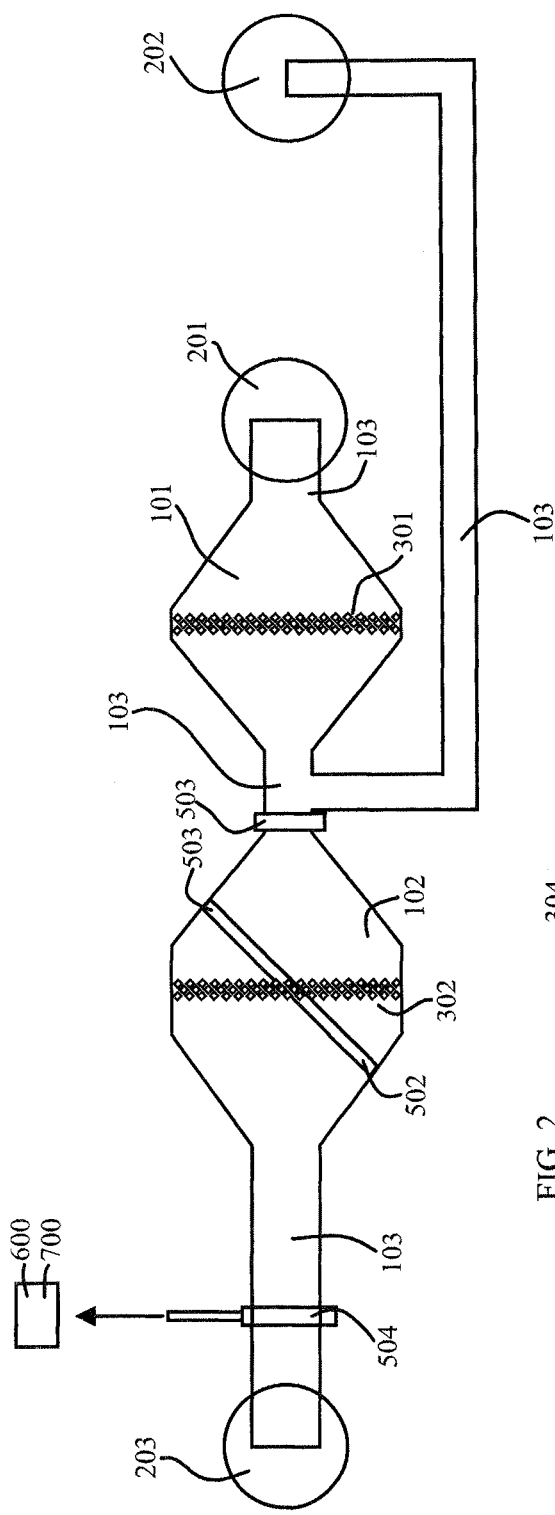
FIG. 2 is a schematic representation of a top view of a microfluidic channel system with two reaction chambers.
Figure 2:
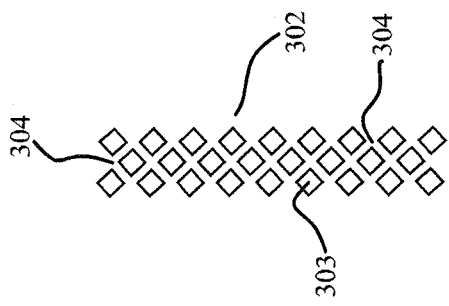

FIG. 2 schematically illustrates a preferred embodiment of the microfluidic channel system seen from above. The microfluidic channel system comprises one or more, preferably two reaction chambers (101 and/or 102) with three sealable liquid connections (201, 202 and/or 203), which are sealable and act as inlets and/or outlets for the liquid flow. In other words, liquid feeding may be carried out from any of the liquid connections (201, 202, and/or 203) and it is also possible to reverse the chosen order and direction of the flow. The reaction chambers (101 and/or 102) are each provided with at least one fluidic pillar filter (301, 302). The pillars of the microfluidic pillar filter consist of pillars or rods, e.g. pillar rods (303) with spacings or interspaces (304) having a size allowing the magnetic microbeads to pass at least one by one. Liquid may be fed through connection (201), which may act as the main feeding channel leading to reaction chamber (101) or the so called bubble chamber, wherein air bubbles are filtered with the microfluidic pillar filter (301). Thereafter, the liquid stream contacts the clusters of magnetic microbeads, which may be manipulated using an externally located magnetic rod (not shown in FIG. 2). It is possible to move the magnetic microbeads back and forth through the microfluidic pillar filter (302) in reaction chamber (102) or through the microfluidic pillar filters (301) in reaction chamber (101) or back and forth through both of the two microfluidic pillars (301) and (302), thereby using both reaction chambers. The presence of three liquid connections enable trapping of the magnetic microbeads in any one of the reaction chambers (101 or 102) behind one of the pillar filters (301 and/or 302) or for example in the channel (103) behind the pillar filter (302) or pillar filter (301), when the liquid is replaced or changed in the system or removed from the system, e.g. through the liquid connection (202). After the introduction or injection of a new, replacing liquid, comprising reagents, buffer or eluting solutions, it is possible to transfer or move the magnetic microbeads back into the newly introduced liquid solution (reagent, washing or eluting solution) present in one of the reaction chambers by switching on the magnetic rod. The magnetic microbeads tend to form clusters and the magnetic particle clusters may be broken with external magnetic rod (not shown in FIG. 2) by moving the external magnetic rod over the pillar filters (301 and/or 302) of the reaction chamber (101 and/or 102). The microfluidic pillar filters (302) in the reaction chamber (102) are used for preventing clustering of magnetic microbeads during reactions and purification or washing. The electric equipment (500) of the microfluidic chip device comprises electric thin film elements (501), which include a heating element (502) and a temperature measurement element (503) are placed across the reaction chamber (102) and high voltage contacts (504), which are placed on both sides of the reaction chamber (102) or on both sides of the microfluidic channel (103). These electric equipment or electric thin film elements (500) may be used for performing e.g. PCR-reactions after the completion of a binding assay between complementary poly- or oligonucleotide sequences and for concentration of the processed reactants comprising either the desired components or target partners or their counterparts, whichever it is desirable to determine of the binding pair, after the desired binding reactions and before the liquid with the processed reactants is allowed to enter the capillary system for separation of the target partners or their counterparts by capillary electrophoresis (CE) (600) followed by recording and detecting (700) said target partners or reactants with appropriate equipment. A further reaction chamber may be placed immediately before the location, wherein the fluidic stream enters the system for fractionation and detection. This further reaction chamber may be used for PCR-cycles, and for providing the target poly- or oligonucleotide sequences or the complementary probe sequences with detectable labels and for diminishing or reducing the background caused by redundant detectable labels by performing two subsequent PCR-cycles, wherein each sequences to be amplified is provided with two universal primers. The reduction is achieved by initiating a first PCR-cycle e with a sequence provided with a detectable label complementary to one of the universal primers and initiating a second PCR-cycle with another sequence which is provided with a sequence complementary to the other universal primer. The now double-stranded probe sequence provided with both detectable and affinity label are thereafter captured or immobilized on magnetic microbeads. The double-stranded probe or hybrid formed, which hybrids are provided with an affinity tag and detectable label by contacting the hybrids with magnetic microbeads, which are forced through the microfluidic pillar filter. The magnetic microbeads are kept behind one of the microfluidic pillar filters, while redundant liquids, reagents, etc are removed through one of the outlets. The steps are thereafter repeated with washing solutions. After this purification the probe or target provided with a detectable label is eluted from the hybrid on the magnetic microbead in a small volume of elution solution. This concentrated solution comprising purified targets or probes to be determined are led into the separation system and for recording.

Figure 3:
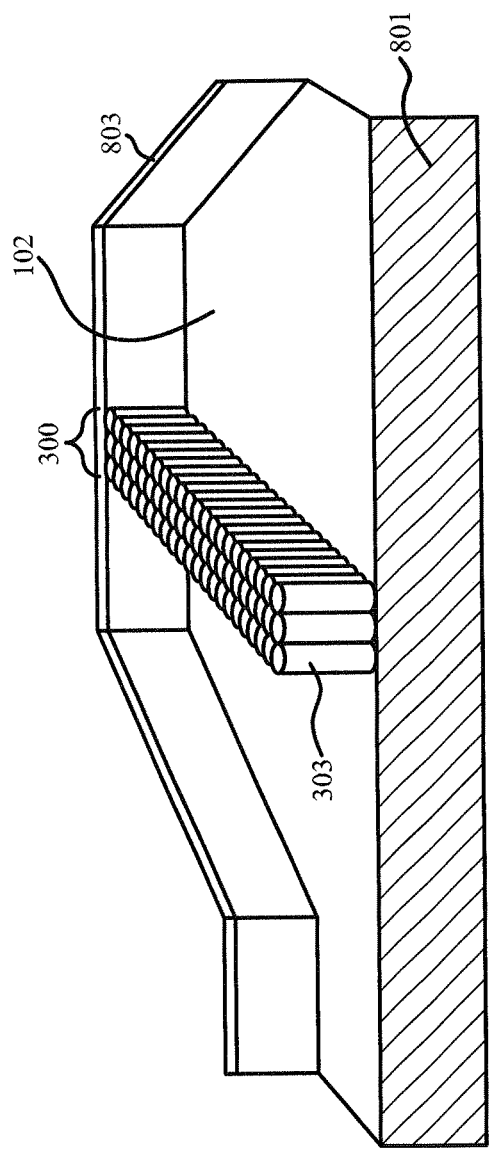
FIG. 3 schematically depicts a three-dimensional perspective view of a latitudinal and longitudinal cross-section of one of the microfluidic reaction chambers demonstrating the construction of a microfluidic pillar filter, which comprises miniature rods.

FIG. 3 depicts a three-dimensional perspective view of a latitudinal and longitudinal cross-section of one of the microfluidic reaction chambers (102) demonstrating the construction of a microfluidic pillar filter (302). The microfluidic channel system with reaction chambers is embedded in the bottom layer (801) of the microfluidic chip device. In a preferred embodiment of the invention the pillar rods (303) have, for example, when in microscale, a height of about 350 µm. They are rectangular, oval or round in shape. One side is about 50 to 100 µm if the pillar rod is rectangular and the diameter is about 50 to 100 µm if the pillar rod is round. The rods are preferably placed with about 25 µm spacings or interspaces, which allow magnetic microbeads having a diameter of e.g. up to 10 to 20 µm to pass through the microfluidic pillar filter. All the dimensions provided herein are only approximate dimensions. Accordingly, the dimensions may vary depending of the size of microfluidic chip device and its dimensions, which may vary between several centimeters down to millimeters. Accordingly, they can be in micro- or macro-size.

Figure 4:
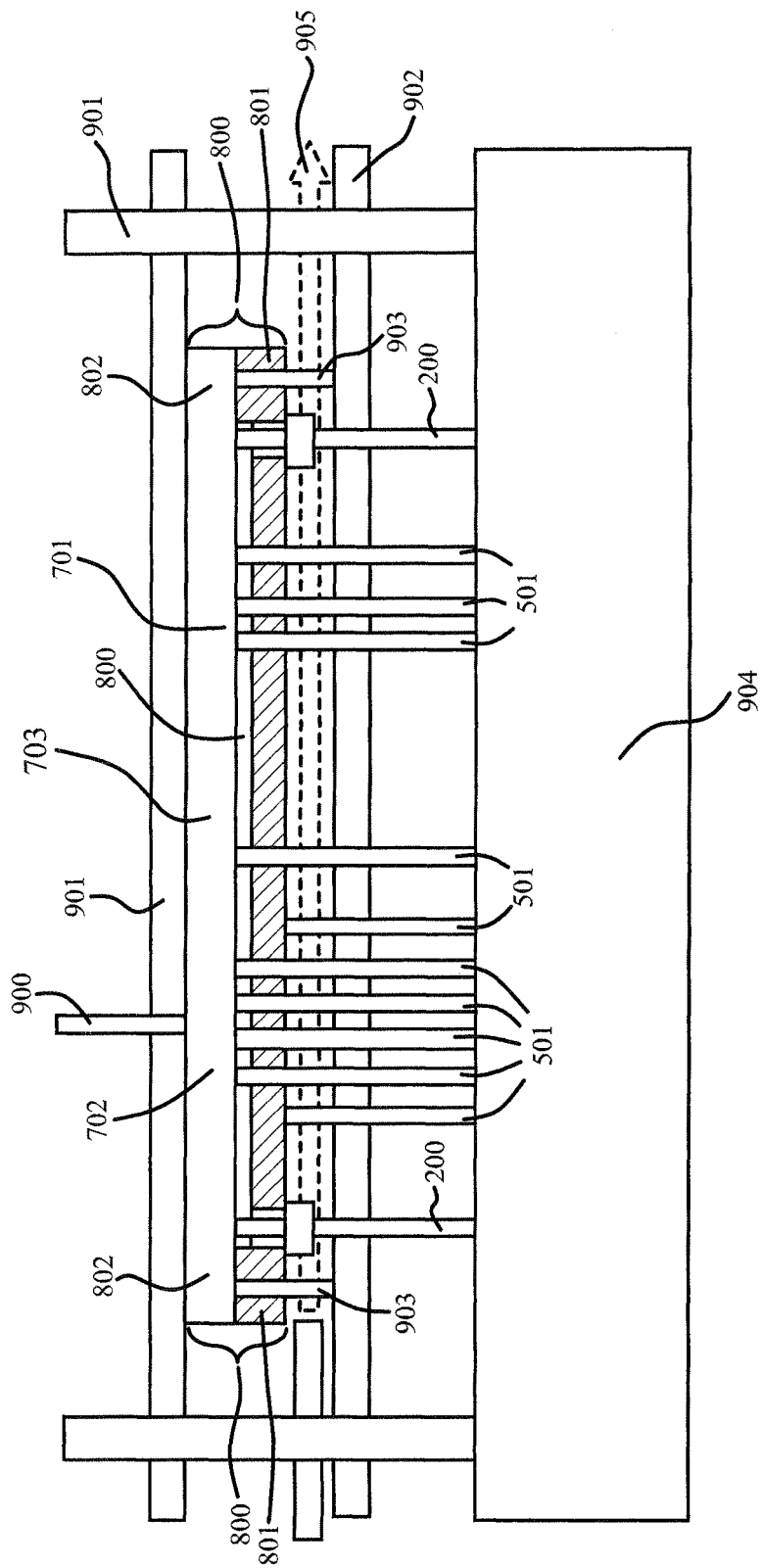
FIG. 4 is a schematic representation of a cross-section of a microfluidic chip device placed on a steering plate with measurement interface and further supported by a docking station.

FIG. 4 is a schematic illustration of the microfluidic chip device (800), which is placed on auxiliary equipment (900) and may be connected to such auxiliary equipment as software-associated automatic or semiautomatic instruments in which the results obtained are collected, and deposited for further calculations and processing. The microfluidic chip device (800) is placed on a steering plate (902) with protruding steering rods (903) connected to a measurement interface (901) and the whole system is supported by a docking station (904). The microfluidic chip device comprises the microfluidic channel system embedded between two layers (801) and (802). The microfluidic channel system (100) includes fluidic connections or couplings (200), magnetic microbeads (401), electric connections or couplings (500), including electric needles and electric pads. The upper layer is transparent and may comprise a fluorescence measurement window (701), means for performing a PCR reaction or concentration (702) of the components in the solution and equipment for performing a capillary electrophoresis (703). In FIG. 4 the liquid connections (200), the steering needles (903) as well as the electric equipment (500) comprising electrical needles (501) or electric thin film elements for heating, for temperature measurement, for providing high voltage concentration, and for conductivity measurement are schematically illustrated as upright rectangular boxes. The microfluidic chip device is placed on a chip steering plate (902) by fitting the chip steering needles or steering rods (903) into the holes on the chip device (not seen in FIG. 4). The magnetic rod is not shown in FIG. 4. An optional air cooling nozzle (905) is shown in FIG. 4. The bottom layer of the microfluidic chip device is preferably a silicon layer (801) supporting the microfluidic channel system (100) in depressions therein and the upper layer (802) is preferably a transparent layer, for example a glass cover with the electric equipment (500) for heating, temperature measurement, provision of high voltage concentration and conductivity measurement. The upper transparent layer also comprises means for performing capillary electrophoresis and means for detection.

FIGS. 5A-5H illustrate different types of microfluidic chip device with different shapes, straight or looped channels and with auxiliary electric and optic equipment placed in various positions on the chip devices.

Figure 5A:
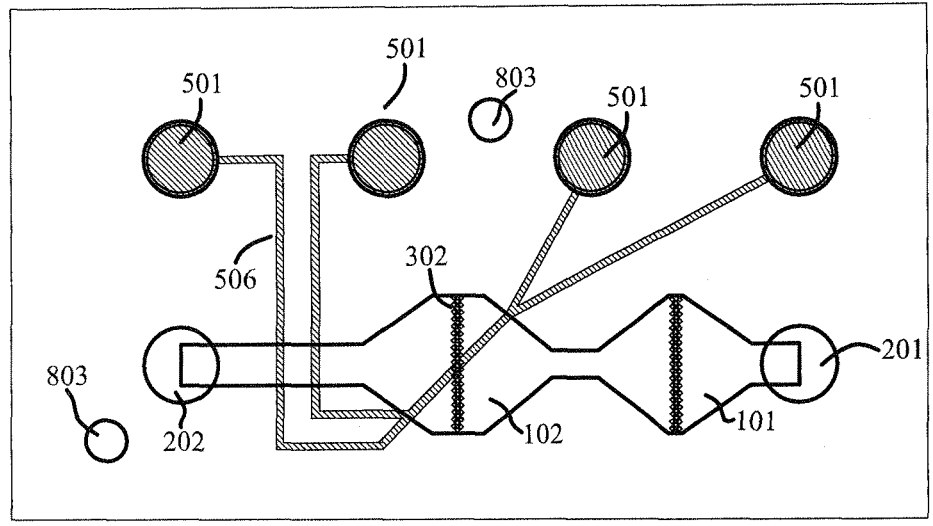
FIG. 5A illustrates a top view of a quadratic microfluidic chip device with two reaction chambers.

FIG. 5A illustrates a top view of a microfluidic chip device with two reaction chamber (101 and 102), fluidic connections (201 and 202) and microfluidic pillar filters (301 and 302). Electrical connections consisting of contact pads or thin film elements (501) and electric wires (506) are shown in FIG. 5A. The microfluidic chip device is provided with holes for the fluidic connections or liquid needles (201 and 202), and with holes (803) for steering needles.

Figure 5B:
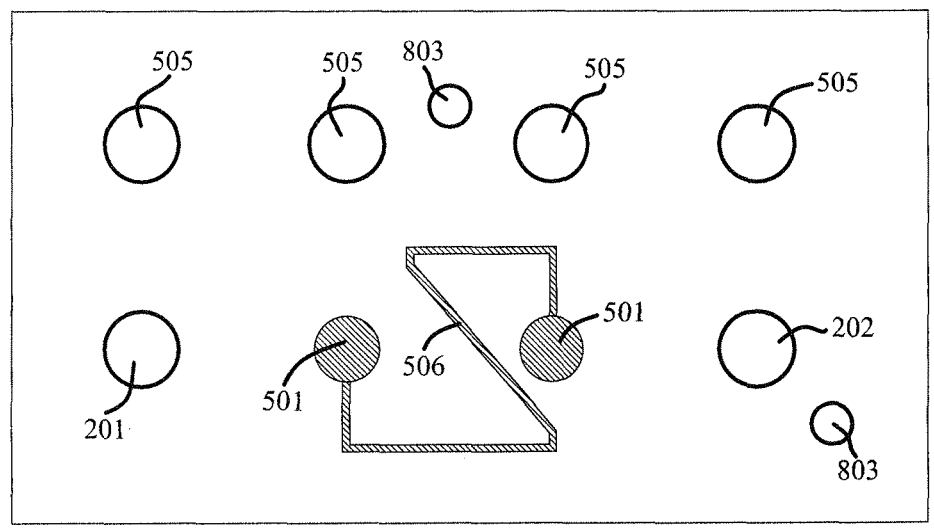
FIG. 5B illustrates a bottom view of the quadratic microfluidic chip device shown in FIG. 5A.

FIG. 5B illustrates a bottom view of a microfluidic chip device the upper view of which is shown in FIG. 5A. The bottom view of the microfluidic chip device shown in FIG. 5B demonstrates contact pads (501) and wires (506) for a heating element located on the lower surface of the silicon layer. The holes for fluidic connections are marked (201, 202). Holes (505) are for the electrical needles.

Figure 5C:
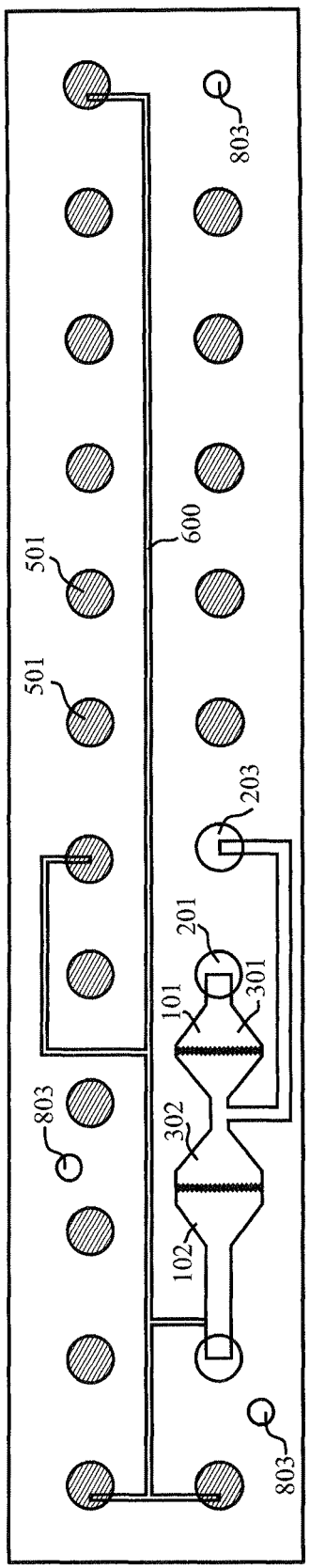
FIG. 5C is a top view of the silicon layer of a rectangular microfluidic chip device with a typical array of electric contact pads, equipment for PCR and a straight channel for capillary electrophoresis.

FIG. 5C depicts the structure of a microfluidic channel system (100) in a microfluidic chip device for performing a polymerase chain reaction-isotachophoresis-capillary electrophoresis (PCR-ITP-CE) with a straight CE channel (600). FIG. 5C illustrates a view of the upper side of the silicon layer. The structure of the reaction chambers (101) acting as bubble filter and the reaction chamber (102) acting as a disintegrator of microbead clusters as well as the electric pads (501) for heating and temperature measurement element are identical in all types of chips. The positions of electric contact pads for the heating and temperature measurement elements may vary. The PCR-ITP-CE chips have thin film elements (501) also for high voltage and conductivity detection. The conductivity detection electrodes have two parallel 20 μm electrodes with 20 μm spacing. The length of the straight CE channel (600) is about 33 mm. The fluidic connections are marked (201, 202 and/or 203) and the pillar filter (301 and/or 302). The holes for the steering wheels are marked (803).

Figure 5D:
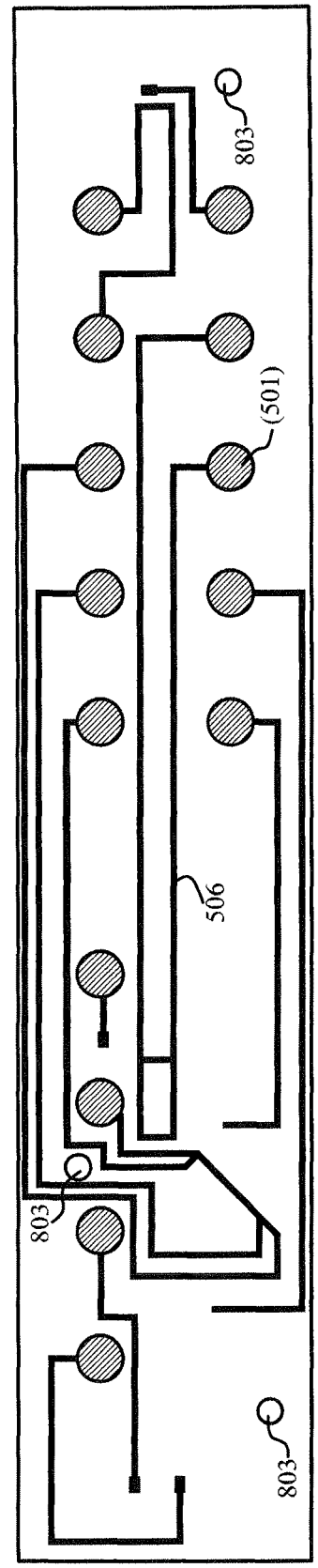
FIG. 5D is a top view of the glass layer of a rectangular microfluidic chip device with an array of electric contact pads differing from that shown in FIG. 5C and equipment for PCR and a straight channel for capillary electrophoresis.

FIG. 5D is a view of the upper side of the glass layer. The glass layer has holes (803) or cavities for the steering needles and electric contact pads (501) or holes for the electric needles (501) and electric wires (506) and the microfluidic channel system (100) with fluidic connections (201, 202, 203), wires (506) and gel electrophoresis, PCR and ITP-channels (600) as indicated in FIG. 5C.

Figure 5E:
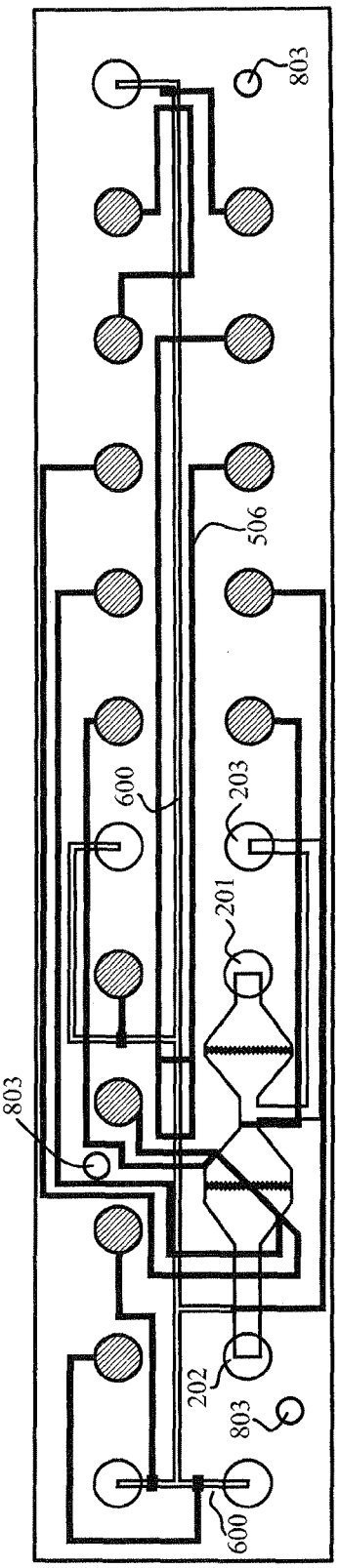
FIG. 5E is a top view of a rectangular microfluidic chip device with an array of electric contact pads differing from those shown in FIGS. 5C and 5D and equipment for PCR and a straight channel for capillary electrophoresis.

FIG. 5E is a view from the upper side of the chip showing equipment in the glass layer and in the silicon layer seen through the glass layer with minor variations.

Figure 5F:
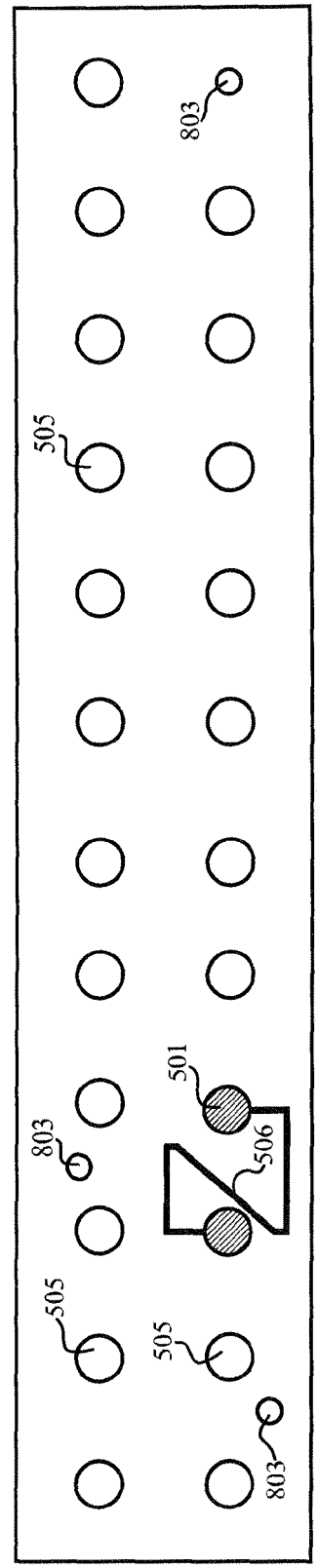
FIG. 5F is a bottom view of a microfluidic chip device corresponding to those shown in FIGS. 5C to 5E with electric contact pad arrays seen on the bottom and equipment for PCR and a straight channel for capillary electrophoresis.

FIG. 5F is a bottom view of the microfluidic chip device shown in FIG. 5E. The PCR-ITP-CE chip has 7 holes for fluidic connections or couplings, 14 holes for electrical couplings (805) and 3 holes for steering needles (803). The location of connections and pads may vary.

Figure 5G:
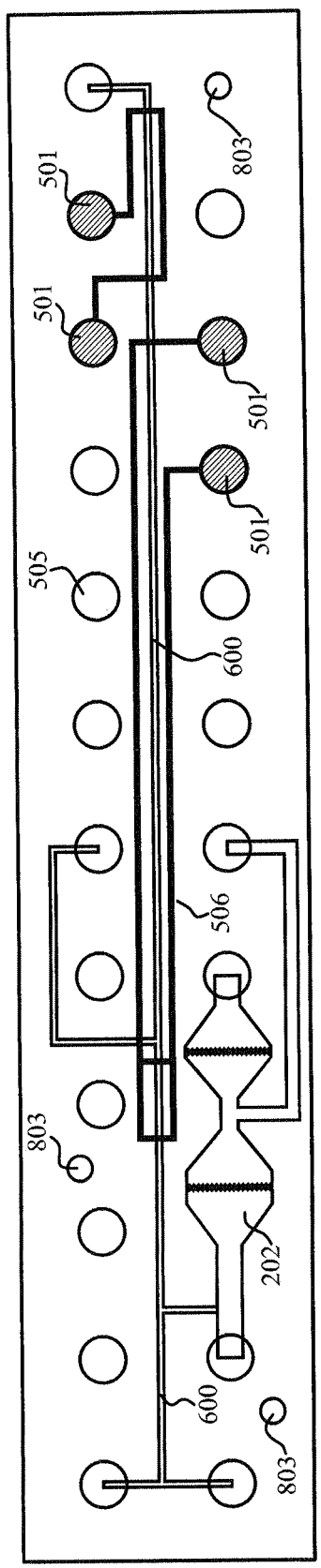
FIG. 5G is a schematic representation of a top view of a rectangular microfluidic chip device with a CE-channel formed as a loop and a microfluidic channel system.
Figure 5H:
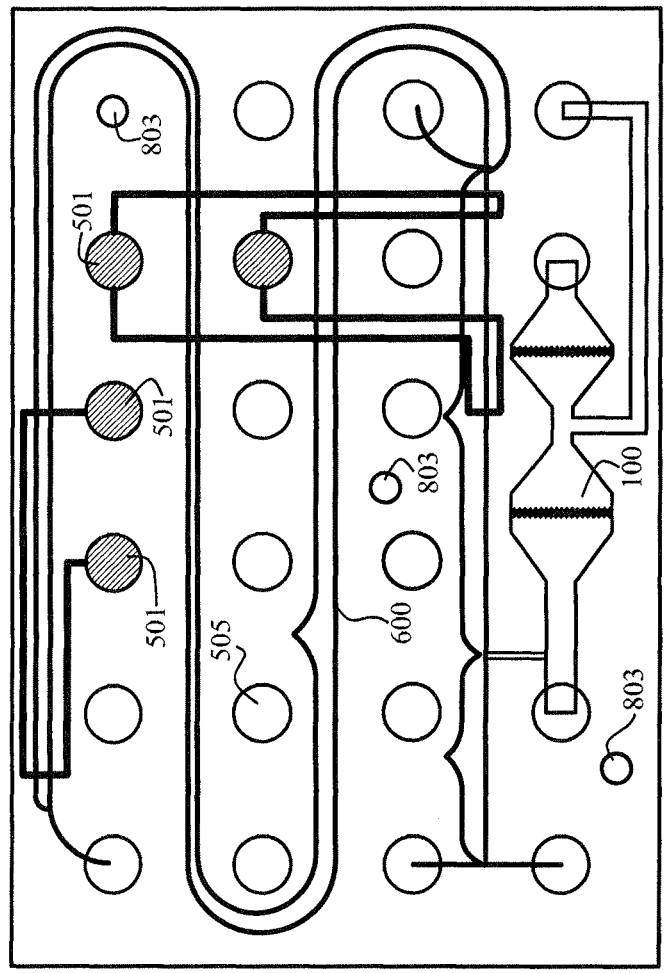
FIG. 5H is a schematic representation of a top view of a quadratic microfluidic chip device with looped CE-capillaries.

FIGS. 5G-5H demonstrate sample injection systems for CE/ITP microfluidic chip devices.

FIG. 5G illustrates a view of the upper side of the silicon layer with a straight CE-channel and a microfluidic channel system, wherein sample injection is carried out with pressure injection, but it is also possible to use electrical injection simultaneously with pressure injection. The pressure injection from the reaction chamber (202) into the sample loop (600) may take place simultaneously with the electrical injection to the sample loop (600). Electric contact pads or electrodes for conductivity detection (505) are shown as well as thin film electric wiring (506). The conductivity measurement electrodes may be used for monitoring the sample injection or the concentration in the CE channel. It is possible by simultaneously applied pressure and/or electrical injection to stop a sample concentrate between two parallel electrode pairs. The sample injection loops of devices in the Figures are 4.1 mm (23 nl) and: 6.3 mm (35 nl), respectively, but may vary depending on the size of the microfluidic chip device The distance from ITP output to the end of CE channel is 22.5 mm. The sample injection loop is placed in double T junction at a position 100 μm from center to center. The distance from the double T to ITP output may preferably be 9.8 mm and the distance from ITP output to the end of CE channel may be 22.5 mm. A sample injection loop with a serpentine shape CE channel, wherein the sample injection loops may be 4.1 mm and 9.6 mm. The distance from ITP output to the end of CE channel may be for example 58 mm.

FIG. 5H illustrates a view of the upper side of the silicon layer with a CE-channel formed as a loop and a microfluidic channel system, wherein sample injection is carried out with pressure injection, is a view of the upper side of the glass layer. The glass layer has holes (803) or cavities for the steering needles.

FIG. 6 is a schematic illustration of a liquid needle (200), which is located in the same for example 3 mm×3 mm matrix as the electrical needles (not shown). The cross-section of the microfluidic chip device is shown in the upper part of the FIG. 6 as the silicon layer (801) and the glass layer (802). The structures of liquid needles and the steering needles are preferably made of steel pipes. A plastic pipe cover steers the liquid needle (200) to the coupling hole on the microfluidic chip device. The plastic pipe steering is based on taper bolt in a steering plate. The liquid needle has a rubber seal in the head of the liquid needle.

Figure 7:
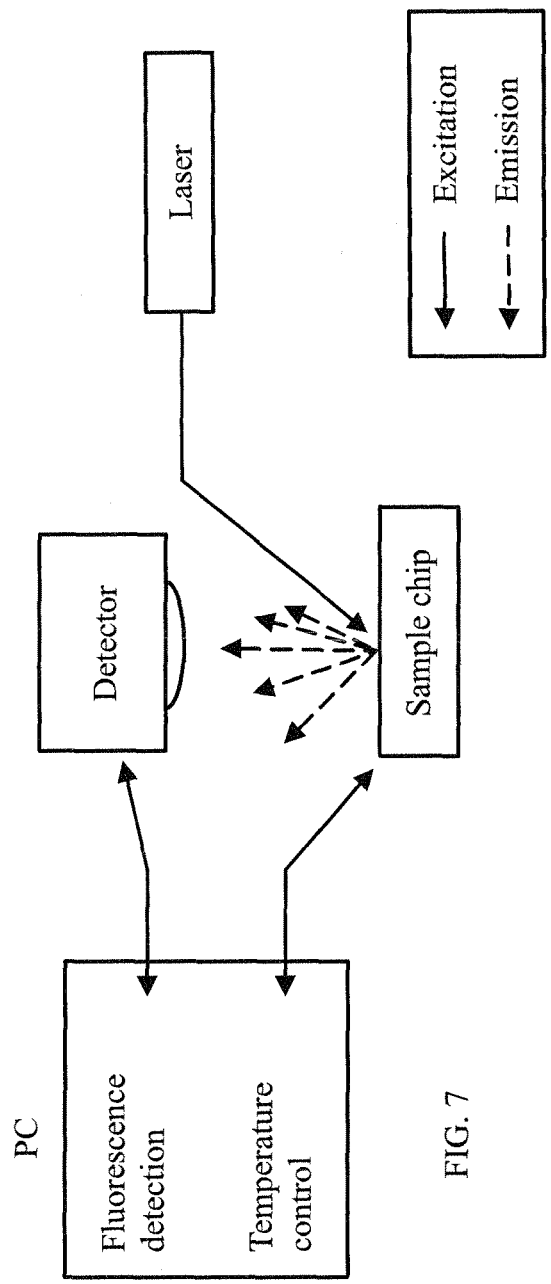
FIG. 7 is a schematic representation of a set up of microfluidic chip device with auxiliary equipment.

FIG. 7 demonstrates the set up of a microfluidic chip measurement set up or a measurement system comprising temperature controlling and fluorescence/conductivity detection. Temperature and fluorescence data is synchronized. Temperature measurement setup is controlled with an AD/DA driver card of PC. The driver card measures the thermistor temperature and controls the heating power of heating element. The fluorescence measurement setup is controlled commercial program (Hamamatsu Wasabi) and LabView software chip measurement setup.

As described above, the microfluidic chip device is a platform, which may include a bottom layer and a top layer, which support the microfluidic channel system between the layers. The upper layer is preferably a transparent glass layer, but quartz or borosilicate may be used. The upper layer may consist of about 200-1000 μm, preferably 400-700 μm, most preferably about 500 μm thick wafers. The surface below the upper layer may be provided with grooves. The tubular channels for transporting the liquid solutions can advantageously be fitted on the grooves located on the side which is below the lower layer. Tubular channels may have associated capillary grooves in the lower layer, but capillary grooves could also be located in the lower surface on the upper layer. The tubular channels, which may be made of glass or inert plastics or other materials such as metal (for example steel), have a diameter of approximately 10-1000 μm, preferably 200-450

μm, most preferably about 350 μm, and are preferably biocompatible or can be made biocompatible.

The lower layer is preferably made of silicon or polymers, but other materials can be used. The lower layer has a thickness of about 200-1000 μm, preferably 400-700 μm, most preferably about 500 μm. The upper and the lower surfaces of the microfluidic chip device may be provided with shaped depressions or grooves, which support the microfluidic channel system. The tubular channels may further include reaction chambers for transporting the liquid solutions, which can advantageously be fitted in the depressions or grooves on the upper side of the lower layer. On the lower side of lower layer electric circuits and electrodes are advantageously soldered and located so as to fit to the junctions connecting the microchip device and the apparatus providing external streams of solutions, electric and magnetic power and leading to separation devices and optic detection instruments.

The top or upper layer and the bottom or lower layer, are joined together in chip level or they are fusion bonded in so called wafer level. Anodic bonding in wafer level and laser bonding in chip level are alternative methods for joining the layers. Glue bonding may be done by screen printing, whereby glue is printed through a screen to the surface of the bottom layer, which preferably is made of silicon. After screen printing, the upper layer, which preferably is a glass layer, may be joined to the silicon bottom layer. The glue or adhesive material may be cured in a furnace or another suitable curing apparatus. In fusion bonding argon gas is used for activation of wafers. After surface activation the top and bottom layers, which may be, for example, silicon and glass wafers, respectively, are joined together. Fusion bonding is strengthened by heating in a furnace having a temperature of about 100-400° C.

In a preferred embodiment of the invention, the microchip may be manufactured substantially as described below, although any other suitable manufacturing method may be used in connection with the present invention. The fabrication of the microchip device of the present invention starts from blank silicon and silica wafers, the diameter of which is preferably about 100 mm, and the thickness of which is preferably approximately 525 μm. The front sides of the silicon wafers are subjected to thermal oxidation, photolithography, oxide etching, Plasma Enhanced Chemical Vapor Deposition (PECVD) silicon nitride deposition, photolithography, PECVD oxide deposition, photolithography, oxide etching and final photolithography. During these processing steps, a three-level plasma etching is conducted to a depth of 75 μm, and 375 μm, respectively and also through the 525 μm silicon wafer. Finally the silicon wafer with the feed-through holes is thermally oxidized to form an electrical insulation.

The silicon layer (801) supports the microfluidic structures including channel and reaction chambers (100) in which the magnetic microbeads (401) are manipulated and the binding assays are carried out. Polymerase chain reaction (PCR), concentration and/or capillary electrophoresis (CE) may be performed in connection with the binding assays to further improve the performance. For PCR and CE the microfluidic chip device is provided by thin film elements (501) for heating. These may be made of molybdenum and provided with a cover layer of Plasma Enhanced Chemical Vapor Deposition (PECVD) and aluminum contact pads. The silicon layer is also provided with thermal oxide electrical insulation, holes for electric contact needles (501), fluidic needles (201 and/or 202, etc) and steering needles or rods (903). The upper glass layer (802) comprises an electric element (501) for temperature measurement, for providing high voltage and conductivity detection. The thin film elements (501) on the upper glass layer (802) are preferably made of platinum and are provided with a cover layer of PECVD oxide. The PECVD oxide can be opened in a contact point or in a measurement point (window).

The back side of the lower layer or the silicon wafer is first coated with molybdenum, which is then patterned by plasma etching after photolithography, to form heaters with contact pads. A cover of oxide is formed using (PECVD), and subsequently the oxide cover is partially etched on to uncover the contact pads.

The bottom layer or silica layer, which preferably is a silicon wafer provided with a patterned photoresistance, which enables a subsequent lift-off procedure of platinum. After the lift-off, the thermistors and conductivity detection circuitry are formed. Thereafter, a cover oxide is formed using PECVD, which is then etched partially to uncover the contact pads for needle contacts through the silicon wafer and to uncover the conductivity detection tips. As a final step, alignment dents are etched to each silica cover of the microchips for steering needles. Then the silica and silicon wafers are sawed into microchips and subsequently bonded with an adhesive.

Utility

The present invention provides accurate assessment of the effects and biological role of binding substances, such as nucleic acids, proteins, antibodies, antigens or enzymes. The rapid and accurate methods for determining diminutive amounts of a plurality target analytes and providing quantitative computer readable results including transcriptional profiles are useful in medicine and pharmaceutical industry. The effects of known and novel drugs on the gene expression of human beings and experimental animals can easily be measure and provide essential knowledge for pharmaceutical and diagnostic industry as well as in health care including hospitals and health centers. The main utility being to provide useful information for health care, treatment modalities, pharmaceutical applications in a form that may be computerized and handled in a numerically exact manner.

The present invention provides a more versatile system for performing miniaturized, rapid and effective hybridization, polymerase chain reaction or amplification assays and immunoassays, which assays all apply a combination of liquid phase and solid phase stages. The rapid and effective purification is achieved in an on-chip device with the microfluidic channel system. The tubular channels of the microfluidic channel systems are provided with enlarged reaction chambers or cavities having microfluidic filters or grids controlled by magnetic rods. The microfluidic filters are capable of disintegrating or disassemble the clusters of magnetic microbeads by forcing the particles through the filter. At the same time the inventors noted that air bubbles, which severely distort results measured in a diminutive step could be avoided by using said pillar filters.

The present invention is related to an analytic microchip device having a multi-channel system for performing rapid and effective solid liquid phase binding assays of one or more binding substances from sample solutions, including cell lysates and mixtures of products obtained for example by combinatorial chemistry.

The microfluidic chip device is useful for increasing the reactive free surface on magnetic microbeads when manipulating the magnetic microbeads in binding assays. Manipulation refers to moving or processing of the target partners and their counterparts on magnetic microbeads. Target binding partners that are manipulated by the methods of the present invention are coupled to their counterparts and together they form binding pairs. The manipulations include transportation or movement, capturing, focusing, enrichment, concentration, aggregation, disintegration, trapping, separation, or isolation. For effective manipulation of target binding partners forming binding pair complexes, the binding pairs and the magnetic force used must be compatible.

The sequential manipulation steps may comprise mixing, concentration, dilution, washing and binding and releasing steps, which facilitate the binding assay in a microfluidic chip device. The steps include reactions, washing, releasing (denaturation, elution), separation, and analysis tasks. The efficiency of said steps depends on effective disintegration of clustering magnetic microbead. The disintegration facilitates dispersion and/or binding of sample components including target binding partners and their counterparts forming binding pair complexes and simultaneous transportation of said components from one part of one reaction chamber to another part of the reaction chamber separated by a microfluidic pillar filter.

The microfluidic channel system is particularly useful for performing assays with analytes which may be binding partners having counterparts, for example antibodies and antigens, which have a specific affinity to each others. Together the binding partner and its counterpart form a binding pair, for example antibodies and antigens or fragments thereof, single-stranded target poly- or oligonucleotide sequences and single-stranded probes, which are complementary to the target poly- or oligonucleotide sequences, may form such complexes. A binding partner and its counterpart, i.e. two binding partners which may form a binding pair, are each separately or alone or as a complex provided with an affinity tag and thereby they may be collected or immobilized on a magnetic microbead covered with another affinity label having affinity to the corresponding affinity tag. Thus the magnetic particles, which have immobilized one binding partner may collect the counterpart which may or may not carry a detectable label of said binding partner and thereby form an immobilized binding pair complex.

Usually the target binding partner is the component which is to be determined from a sample. It is the desired component or the component of interest in the assay. It can be processed, e.g. isolated before entering the microfluidic chip device, but it can be directly introduced, if it is soluble or solubilizable in the sample media, buffer solution or eluting solution used in the binding assay.

The target binding partner can be any organic or inorganic molecule, which has a specific affinity for another molecule, which is its counterpart. Useful target binding partners can be amino acids, peptides, proteins, glycoproteins, lipoproteins, glycolipoproteins, lipids, fats, sterols, sugars, carbohydrates, nucleic acid molecules, small organic molecules, or more complex organic molecules. The target partner can also be molecular complexes and inorganic molecules or ions. The target binding partners may be intracellular target partners obtained from cells, cytoplasm or matrix of cellular organelles, which have been lysed.

The reaction conditions for immunoassays, hybridization reactions, etc can be found in text books and laboratory handbooks. If a plurality of analytes and reagents are used. It is most convenient to use standardized conditions for the different reactants.

A binding assay records a result obtained from sample processing and includes any assays comprising adsorption and desorption reactions applying affinity capturing. Generally, a binding assay determines the presence, amount, or activity of one or a plurality of target binding partner in a sample. Adsorption includes binding, coupling or capturing and is a characteristic step in the binding assay and facilitates the purification and final separation and detection of one or a plurality of target binding partners from a sample.

The binding assay of the present invention comprises sequential steps including adsorption and desorption reactions with intermediate washing, which can be repeated with different reagents or by introducing a new sample. In an integrated microfluidic chip device of the present invention, the different steps are performed sequentially to obtain a final result. When two tasks are performed sequentially, the second task uses one or a plurality of products of the first task. In the present invention the product means a target binding partner in the sample that has been immobilized on a magnetic microbead and purified, or concentrated in the first step, or has became bound to a reagent which is also bound to said magnetic microbead.

Target binding partners are immobilized on magnetic microbeads and thereafter allowed to react with their counterparts to form binding pair complexes or they are allowed to react with their counterparts, which have been previously attached to magnetic particles or are attachable to the magnetic beads. The target binding partners and their counterparts as well as appropriate affinity tags and detection labels are simultaneously allowed to contact the magnetic microbeads, thereby the reactions between the binding partners take place in solution and the binding pairs formed are immobilized as complexes.

Without applying the method of the present invention about 5%, 10%, 20%, 30%, 40%, or 50% of the target partners are immobilized with their binding pairs on the magnetic particle. By manipulating the magnetic particles by forcing them through the microfluidic pillar filter the formation of immobilized binding pairs may be increased up to about 60%, 70%, 80%, 90%, or 100%

In the present invention immobilized means that something is coupled, captured or bound to a solid support, the magnetic microbead. A target binding partner and its counterpart may for example be coupled to a magnetic microbead by specific or nonspecific binding. The binding can be covalent or non-covalent, reversible or irreversible, preferably affinity pairs, such as biotin avidin and biotin streptavidin are used to facilitate binding between on binding partner and the magnetic microbead.

In contrast to immobilized the term trapped means that a mechanical barrier is used to prevent the magnetic microbead with the immobilized targets and reagents from moving.

In the present invention separation means a process in which a plurality of target partners or their binding pairs present in a sample are spatially separated from one or more other target partners using chromatographic equipment for separation, applying capillary electrophoresis, gravity, mass flow, dielectrophoretic forces, and electromagnetic forces.

A target binding partner is one of two different molecules having an area on the surface or in a cavity in the three dimensional structure of the molecule, which cavity specifically binds to and is thereby defined as complementary with a particular spatial and polar organization of the other molecule. A specific target partner can be a member of an immunological pair such as antigen-antibody, biotin-avidin or biotin streptavidin, ligand-receptor, nucleic acid duplexes, DNA-DNA, DNA-RNA, RNA-RNA, and the like. It is to be noted that the binding partners are soluble in a water-based solution, but have affinity for each other and have affinity for the magnetic microbeads or can be provided with a groups, which has affinity for the microbeads or a member of an affinity pair attached on the microbead.

A water-based solution is a biological sample solution, a physiological buffer, biocompatible liquids used as hybridization solutions, denaturating solution or for elution in the gel electrophoresis. Laboratory handbooks provide a multitude of useful water-based solutions. By changing temperature, ph conditions and ingredients in said solutions it is possible to alternating adsorption and desorption reactions on the magnetic microbeads or beads.

Nucleic acid molecules are polynucleotide sequences. A nucleic acid molecule can be DNA, RNA, or a combination of both. A nucleic acid molecule can also include sugars other than ribose and deoxyribose incorporated into the backbone. The backbone can be other than those in DNA or RNA. Locked nucleosides form LNA and peptide backbones form PNA and comprise nucleotide bases that are naturally occurring or that do not occur in nature. A nucleic acid sequence can have linkages other than phosphodiester linkages. A nucleic acid sequence can be a peptide nucleic acid molecule, in which nucleotide bases are linked to a peptide backbone. A nucleic acid sequence can be of any length, and can be single-stranded, double-stranded, or triple-stranded.

Standard binding assays include those that rely on nucleic acid hybridization to detect specific nucleic acid sequences, those that rely on antibody binding to entities, and those that rely on ligands binding to receptors.

In a conventional binding assay, a detectable label is generally needed in order to enable determination, measurement or recording of the result. A detectable label is a compound or molecule that can be detected or can generate a measurable signal. Useful labels are fluorescence, radioactivity, color, or chemiluminescence. Preferred are fluorescent labels, which are commercially available and include Cy-5, phycoerythrin, phycocyanin, allophycocyanin, FITC, rhodamine, or lanthanides; and by fluorescent proteins such as green fluorescent protein (GFP). These and any other suitable labels may be used in accordance with the present invention. The reagent can be prelabeled, but methods exist by which the unlabeled reactants may be labeled after the reaction. In some cases this is the preferred method, by which steric hindrances caused by the labels can be avoided.

The microchip device with the microfluidic channel system may be used for performing transcript analysis by the aid of affinity capturing (TRAC) and for determining the amounts of target polynucleotide sequences and nucleotide variations therein, e.g. from a cell lysate.

According to one aspect of the invention the microchip device may be used in a binding assay, wherein first a buffer solution comprising magnetic particles covered by counterparts, e.g. a mixture of known antigens or antibodies, of the binding substance, e.g. antibodies or antigens, respectively, is injected into the tubular microfluidic channel system (100) and is transferred to the a reaction chamber (101, 102) with microfluidic pillar filters or grids (301, 302) by the stream of solution. A sample solution containing a mixture of the binding partners, e.g. the respective antibodies or antigens, is injected to the tubular microfluidic channel and is mixed with its counterparts attached on the magnetic microbeads. The inlets are closed by externally controlled mechanical valves. The clustering magnetic microbeads may be disintegrated by forcing them through the microfluidic pillar filters to another reaction chamber by the aid of magnetic rods. This transfer back and forth may be repeated one or more times. Thereby a thorough mixing of the reagents is also achieved. After a suitable time, which ensures a complete reaction between the binding substance and its counterpart, the solution is removed through one of the outlets, while the magnetic particles are retained in one of the chambers behind the filter when the magnetic forces or rods are switched off by raising the magnetic rod up. The tubular microchannels are opened with external mechanical valves and a stream of washing solution is injected through the tubular microfluidic channel to the reaction chamber, wherein the magnetic microbeads covered by the complexes of binding partners and their counterparts are washed free from unbound sample and reagents by forcing the microbead through the filters and by trapping them during drainage of the solutions. This procedure may be repeated one or more times and finally the binding substances are released using, for example a buffer solution capable of releasing the binding partner from its counterpart, which is retained in the reaction chamber with the magnetic microbeads. The releasing buffer solution preferably is a solution, which can be used for elution in the subsequent capillary or gel electrophoresis, which separates the binding substances, before recording their optical properties. The magnetic particles with the captured counterparts of the binding substances are retained and can after washing be reused by adding another sample from which the same multi-analysis can be performed.

According to a further aspect of the invention, the use of the microchip is demonstrated as a method for quantifying expressed target mRNA. In a still further exemplified aspect of the invention the microchip device of the present invention is applied for determining the amount of target polynucleotide sequences and nucleotide variations therein.

A sample is any fluid from which components are to be separated or analyzed. A sample can be from any source, such as an organism, group of organisms from the same or different species, the cells of which are subjected or have been subjected to lysis. It may be an extract from the environment, as soil, food, buildings or any other solid source. In a microfluidic system the sample should be in liquid form as a solution or an extract, for example a liquid extract of a soil or food sample, an extract of a throat or genital swab, or an extract of a fecal sample. Blood samples are preferably centrifuged, lysed, filtered, extracted, or otherwise treated blood sample, including a blood samples to which one or more reagents such as anticoagulants or stabilizers have been added. The sample can be an unprocessed or a processed sample.

The processing of a sample starts with sample preparation, which may include the disruption of a cell or tissue sample to release the target partners or components to be determined. Sample preparation may involve a crude separation or purification including separation of polynucleotide sequences and proteins, but a cell sample may be introduced directly into the microfluidic channel system, wherein it subjected to lysis, or it may be introduced after external lysis. The sample processing usually includes separation of components of a sample, but in the present invention the target partners or components of the sample are processed together and the separation and identification of the target partners is carried out the adsorption and desorption reactions. The disruption may include lysis, denaturation rendering for example double-stranded nucleic acid sequences or fragments thereof single-stranded, chemical modification, or binding of components to reagents. A processing step can act on one target partner in the sample by releasing, exposing, modifying or generate another type of component, e.g. the binding pair of target partner that can be used in a further processing or analysis. The tasks include measurement and calculation. For example, lysis of one or more cells or tissues can be a first processing step to release nucleic acids that can be separated in a further step task and detected in a subsequent analysis step. Binding or coupling can be a step in a processing task, where binding or coupling, particularly the coupling of a target partner in a sample to its binding pair present on a microbead facilitates the separation, transportation, immobilization, isolation, focusing, concentration, enrichment, structural alteration, or at least partial purification of one or a plurality of target partners of a sample. In conventional prior art methods mixing is a necessary task for facilitating the binding, separation, transportation, concentration, structural alteration, or purification of one or more target partners in a sample. Mixing is a problem in a microfluidic channel system, which does not allow introduction of sufficiently effective forces. In the present invention a sufficient mixing is provided by forcing magnetic microbeads through the pillar filter by switching a magnetic rod on and off.

The present invention relates to methods for performing binding assays using magnetic microbeads. The target binding partner is a component, in principle it can be any constituent in a water based liquid sample, which has a specific affinity for and binds to another component when contacted with its binding pair.

The method may be applied for PCR-cycles, which can be carried out in the fluidic channel or in reaction chamber and for providing the target polynucleotide sequences or the probe sequences with detectable labels and for diminishing the background noise by performing two subsequent PCR-cycles with a probe sequences having two universal primers by initiating the PCR-cycle e with a sequence provided with a detectable label complementary to one of the universal primers and initiating a second PCR-cycle with another sequence which is provided with a sequence complementary to the other universal primer. Capturing the hybrid formed, which hybrids are provided with an affinity tag and detectable label by contacting the hybrids with magnetic microbeads, forcing the magnetic microbeads through the microfluidic pillar filter and keeping the microbeads behind a microfluidic pillar filter while removing the redundant liquids, repeating the steps with washing solutions and eluting the probe or target provided with a detectable label from the hybrid in a small volume of elution solution and leading said solution into the separation system and for recording.

In the present invention, at least three main types of microfluidic chip devices are disclosed. The three different types of microchip devices include microchip devices with possibilities for carrying out binding assays, binding assays with a polymerase chain reaction (PCR chips); microchip devices with possibilities to carry out both binding assays with PCR and capillary electrophoresis (CE) with a straight CE channel or a serpentine CE channel. As a common feature all three types of microchip devices have at least two different fluidic couplings, including but not limited to side couplings and liquid needles.

The use of the microfluidic chip device for performing a miniaturized transcript analysis by aid of affinity capturing (TRAC) assay is described below. Conventional TRAC assays are described in the European Patent Nos. 1352097 and 1537238. One object of a TRAC assays is to determine from a sample solution the relative amounts of a plurality of expressed mRNA.

The method may comprise the following steps:

(a) contacting a liquid stream comprising a sample solution containing a plurality of sample soluble target mRNA, poly (T) probes with affinity tags, preferably biotin tags and a plurality of stable single stranded probe sequences labeled with detectable labels, preferably fluorophors and having sequences complementary to the target mRNA, the relative amounts of which are to be determined, and wherein each of the plurality of probe sequences have sizes or masses which have distinct sizes, with magnetic microbeads (401) by introducing said liquid stream into the microfluidic channel system (100) comprising two reaction chambers (101, 102) through connection (201) acting as an inlet and through microfluidic pillar filter (301) to remove bubbles a liquid stream and subsequently sealing fluidic connections (201, 202, and 203);

(b) allowing immobilization and hybridization reactions to take place in favorable conditions for a time sufficient to provide immobilized target mRNA-probe complexes on the magnetic microbeads by transferring the magnetic microbeads back and for the through at least one of the microfluidic pillar filters (301 or 302);

(c) trapping the magnetic microbeads with the immobilized (captured) target mRNA-probe complexes (hybrids) on the microfluidic pillar filter (302) by switching off the magnetic rod (402) and removing the liquid stream through the liquid connection (202) and closing connection (202);

(d) purifying the magnetic microbeads with the immobilized target mRNA-probe complexes by introducing a new liquid stream containing a washing solution favoring hybridization by switching on the magnetic rod (402) and forcing the magnetic microbeads back and forth through at least one of the microfluidic pillar filters (301, 302);

(e) trapping the magnetic microbeads with the immobilized target mRNA-probe complexes on or behind the microfluidic pillar filter (302) by switching off the magnetic rod (402) and removing the liquid stream through the liquid connection (202) and closing connection (202);

(f) releasing the probes from the target mRNA-probe complexes immobilized on the magnetic microbeads by introducing a new liquid stream containing a denaturating solution rendering the double stranded complex single stranded and by switching on the magnetic rod (402) and forcing the magnetic microbeads back and forth through at least one of the microfluidic pillar filters (301, 302) allowing the denaturation take place for a time sufficient to release the probes;

(g) trapping the magnetic microbeads with the immobilized target mRNA on the microfluidic pillar filter (302) by switching off the magnetic rod (402) and introducing the liquid stream containing the probes into a microfluidic channel outlet for optional amplification and/or concentration before allowing the probes to enter the separation equipment and performing a capillary electrophoresis for separating and discriminating the plurality of probes from each other and graphically recording the intensity of the detectable label (fluorescence) of each of the probes and by using software-associated automatic or semiautomatic instruments calculating the amount of the probes from the graphically recorded peaks (202) which corresponds to the relative amount of target mRNA present in the sample solution.

By adding a further step to the method described above relative amounts of expressed mRNA and nucleotide variations therein can be determined. The method is a miniaturized version of the method described in the International Patent Application No. WO 2008/102057 (PCT/FI2008/050074), which is incorporated herein by reference in its entirety.

In the additional step, the oligonucleotide probes which are immobilized and purified in step (d) are elongated in their 3'-terminal end using the 5'-terminal end of the target mRNA as a template; by introducing after step (e) through the liquid connection (201) and the microfluidic pillar (301) a buffer solution comprising an enzyme, such as a polymerase or reverse transcriptase, which in the presence of at least one deoxynucleotide, such as dTTP, dATP, dCTP or dGTP or at least one dideoxynucleotide such as ddTTP, ddATP, ddCTP or ddGTP is capable of elongating the probe using the target mRNA as a probe. By switching on the magnetic rod (402) and forcing the magnetic microbeads with purified immobilized target mRNA-probe complexes through the microfluidic pillar filter (302), the elongation reaction is allowed to take place for a sufficient time and in conditions favouring elongation reaction. After trapping and purifying the magnetic microbeads, the probes with or without elongations are released, separated and recorded. From the peaks in the graphically recorded results and using appropriate controls the relative amounts of the probes with or without elongations can be calculated and the amounts of the complementary target mRNA and nucleotide variations in said mRNA, which have hybridized with the original probes, can be evaluated.

As said above the released probes may be amplified in the microfluidic chip device before they are separated by e.g. capillary electrophoresis and the intensity of the label is recorded.

According to another aspect of the invention, the microfluidic chip device of the present invention may be used in methods for carrying out a PCR reaction. This PCR-reaction may be carried out before transferring the probe polynucleotides, which have hybridized to the analyte sequences and which have been purified when captured on the solid support, and thereby separated from unreacted sequences in the sample.

The magnetic rod is let down to the reaction chamber (101) and a solution containing magnetic microbead is fed in from the liquid connection (201). The magnetic microbeads are washed and a DNA sample is added from the liquid connection (201). The magnetic microbeads are moved from one chamber to another by moving the magnetic rod from the reaction chamber (102) to the bubble filter chamber (101). A PCR amplification mixture is added from liquid connection (201) and the magnetic microbeads are moved from the bubble filter chamber (101) to the reaction chamber (102) and channel, wherein the PCR reaction takes place and moves them to the bubble filter chamber (101). The solution is fed or added from liquid connection (201) and the magnetic microbeads are moved by the magnetic rod (402) from bubble filter chamber to reaction chamber (102) and the channel (103). Thereafter, the DNA is eluted from the magnetic microbeads, which are moved by the magnetic rod to bubble filter chamber (101). An optional electrical pre-concentration is carried out with the high voltage electrodes (505). A separation electrolyte is transferred to CE/ITP channel (600). The sample is injection from inlet (203) to CE/ITP: 2 (600). An optional ITP pre-concentration is carried out and the DNA identification is carried out with CE separation. The DNA identification in ITP/CE channel may be carried out with at least five different DNA identification procedures in the ITP/CE channel.

1. The identification is carried out by concentration of the sample with ITP before CE separation. The ITP is carried out in a side channel of the main CE channel. The CE separation is carried out after the ITP concentration.
2. Simultaneously pressure/electrical injection from PCR cavity. Concentrated sample between parallel conductivity electrodes in an injection loop present in the microfluidic chip device straight or in a loop channel in the microfluidic chip device shown in FIGS. 5A-5H. The CE separation is carried out after the sample injection.
3. The sample injection toward the gel solution interface is carried out in sample loop (600) in the microfluidic chip devices shown in FIGS. 5A-5H. The CE separation is carried out in a buffer solution.
4. Gel electrophoresis is carried out with ITP concentration. The whole CE channel is filled with gel solution. The CE separation is carried out in gel solution.
5. Sample injection is carried out in double T injection microfluidic chip device shown in FIGS. 5E-5H. The CE separation is carried out after sample injection.

It will, of course, be appreciated that the above description has been given by way of example only and that modifications in detail may be made within the scope of the present invention.

The invention is capable of considerable modification, alteration, and equivalents in form and function, as will occur to those ordinarily skilled in the pertinent arts having the benefit of this disclosure.

While the present invention has been described for what are presently considered the preferred embodiments, the invention is not so limited. To the contrary, the invention is intended to cover various modifications and equivalent arrangements included within the spirit and scope of the detailed description provided above.

What is claimed:

1. A microfluidic chip device, comprising
a microfluidic channel system comprising at least two reaction chambers interconnected with a channel having three or more liquid connections, the channel comprising sealable fluidic connections on both sides of the at least two reaction chambers, wherein the sealable fluidic connections act as inlets and/or outlets for a liquid stream,
magnetic microbeads provided within at least one reaction chamber of the microfluidic channel system,
wherein each reaction chamber comprises at least one microfluidic pillar filter within the reaction chamber, wherein the microfluidic pillar filter comprises pillar rods having interspaces sized to allow the magnetic microbeads to pass the interspaces one by one, and
wherein the at least one microfluidic pillar filter filters bubbles formed in the liquid streams, and disintegrates clusters of magnetic microbeads.

2. The microfluidic chip device according to claim 1, wherein the microfluidic channel system further comprises equipment selected from the group consisting of magnetic equipment, electric equipment, optical equipment, and combinations thereof.

3. The microfluidic chip device according to claim 2, wherein the equipment is integrated or externally connected.

4. The microfluidic chip device according to claim 3, wherein the equipment is used for carrying out techniques selected from the group consisting of isolation, purification, concentration, binding assays, PCR, and reduction of background.

5. The microfluidic chip device according to claim 2, wherein the equipment is magnetic equipment, and the magnetic equipment comprises one or more externally manipulatable magnetic rods.

6. The microfluidic chip device according to claim 2, wherein the equipment is electric equipment, and the electric equipment comprises electric connections selected from the group consisting of electric needles and electric thin film elements.

7. The microfluidic chip device according to claim 6, wherein the electric thin film elements are selected from the group consisting of heating elements, temperature measurement elements, high voltage elements, conductivity measurement elements, and combinations thereof.

8. The microfluidic chip device according to claim 1, wherein the microfluidic channel system further comprises integrated or externally connected fractionation and separation equipment.

9. The microfluidic chip device according to claim 8, wherein the fractionation and separation equipment comprises straight or looped channels for carrying out capillary electrophoresis with or without isatachophoresis pre-separation or mass spectrometry.

10. The microfluidic chip device according to claim 1, wherein the microfluidic channel system further comprises integrated or externally connected detector equipment selected from the group consisting of equipment for measuring fluorescence, equipment for measuring UV/IS absorption, equipment for measuring IR, equipment for measuring conductivity, equipment for measuring refraction index, and a mass spectrometer.

11. The microfluidic chip device according to claim 1, wherein the sealable fluidic connections are fluidic connectors having seals preventing leakage.

12. The microfluidic chip device according to claim 1, wherein the microfluidic chip device comprises two layers.

13. The microfluidic chip device according to claim 12, wherein the microfluidic chip device comprises a bottom layer and a top layer with holes.

14. The microfluidic chip device according to claim 13, wherein the microfluidic chip device is contacted to external detector equipment through a measurement interface, and a steering plate with steering rods fitting in the holes on the microfluidic chip device.

15. The microfluidic chip device according to claim 2, wherein the microfluidic chip device and external equipment are placed on a docking platform.

* * * * *

UNITED STATES PATENT AND TRADEMARK OFFICE
CERTIFICATE OF CORRECTION

| | | |
|---|---|---|
| PATENT NO. | : 8,895,292 B2 | Page 1 of 1 |
| APPLICATION NO. | : 12/421252 | |
| DATED | : November 25, 2014 | |
| INVENTOR(S) | : Söderlund et al. | |

It is certified that error appears in the above-identified patent and that said Letters Patent is hereby corrected as shown below:

On the title page

Delete:

"(75)  Inventors: Hans Söderlund, Espoo (FI); Ari Hokkanen, Espoo (FI); Kari Kataja, Espoo (FI); Ingmar Stuns, Espoo (FI); Kai Kolari, Espoo (FI); Heli Siren, Espoo (FI); Stella Rovio, Espoo (FI); Reetta Satokari, Espoo (FI), Jan Rautio, Espoo (FI)"

Insert:

--(75)  Inventors: Hans Söderlund, Espoo (FI); Ari Hokkanen, Espoo (FI); Kari Kataja, Espoo (FI); Ingmar Stuns, Espoo (FI); Kai Kolari, Espoo (FI); Heli Siren, Espoo (FI); Stella Rovio, Espoo (FI); Reetta Satokari, Espoo (FI), <u>Jari</u> Rautio, Espoo (FI)--

Signed and Sealed this
Twenty-fourth Day of March, 2015

Michelle K. Lee
*Director of the United States Patent and Trademark Office*